US012661487B2

(12) United States Patent
Andriola et al.

(10) Patent No.: US 12,661,487 B2
(45) Date of Patent: Jun. 23, 2026

(54) ANTENNA ASSEMBLIES FOR MEDICAL SYSTEMS AND ASSOCIATED SYSTEMS AND METHODS

(71) Applicant: Shifamed Holdings, LLC, Campbell, CA (US)

(72) Inventors: Peter Andriola, Castro Valley, CA (US); Brian Fahey, Menlo Park, CA (US); Shahn Sage, Clear Lake, MN (US); Eric N. Rudie, Maple Grove, MN (US)

(73) Assignee: Shifamed Holdings, LLC, Campbell, CA (US)

( * ) Notice: Subject to any disclaimer, the term of this patent is extended or adjusted under 35 U.S.C. 154(b) by 347 days.

(21) Appl. No.: 18/458,885

(22) Filed: Aug. 30, 2023

(65) Prior Publication Data

US 2023/0405290 A1     Dec. 21, 2023

Related U.S. Application Data

(63) Continuation-in-part of application No. PCT/US2022/034995, filed on Jun. 24, 2022.
(Continued)

(51) Int. Cl.
*A61M 27/00*     (2006.01)
*H01Q 1/27*     (2006.01)
*H01Q 1/36*     (2006.01)

(52) U.S. Cl.
CPC .......... *A61M 27/002* (2013.01); *H01Q 1/273* (2013.01); *H01Q 1/362* (2013.01);
(Continued)

(58) Field of Classification Search
CPC .......... A61B 2017/00606; A61B 2017/00575; A61B 17/0057; A61B 2017/00243;
(Continued)

(56) References Cited

U.S. PATENT DOCUMENTS 3,874,388 A     4/1975 King et al.
4,369,783 A *  1/1983 Hiller ...................... A61D 7/00
                                                              604/11
(Continued)

FOREIGN PATENT DOCUMENTS

AU     2005211243     8/2005
AU     2010344182     8/2012
(Continued)

OTHER PUBLICATIONS

Extended European Search Report received for Application No. 20896031.0, Applicant: Shifamed Holdings, LLC; Date of Mailing: Dec. 7, 2023; 11 pages.
(Continued)

*Primary Examiner* — Adam Marcetich
(74) *Attorney, Agent, or Firm* — Perkins Coie LLP

(57)     ABSTRACT

The present technology is directed to implantable medical systems that can include a first implantable device, a second implantable device, and a communication assembly that extends between and physically couples the first device and the second device. The first device can include one or more first electronic components, and the second device can include one or more second electronic components. The communication assembly can include (a) one or more first wires that are configured to wirelessly receive data from, and/or wirelessly transmit data to, a third device positioned external to the patient, and (b) one or more second wires that are configured to conductively transfer power between the first electronic components and the second electronic components. In some embodiments, the one or more first wires have a helical configuration, and the one or more second wires have a linear configuration and extend within the one or more first wires.

16 Claims, 5 Drawing Sheets

Related U.S. Application Data

(60) Provisional application No. 63/215,309, filed on Jun. 25, 2021.

(52) U.S. Cl.
CPC . *A61M 2205/0266* (2013.01); *A61M 2205/04* (2013.01); *A61M 2205/3303* (2013.01); *A61M 2205/3327* (2013.01); *A61M 2205/3523* (2013.01); *A61M 2205/3592* (2013.01); *A61M 2205/50* (2013.01); *A61M 2205/8206* (2013.01); *A61M 2205/8243* (2013.01); *A61M 2210/125* (2013.01)

(58) Field of Classification Search
CPC ...... A61B 2017/00247; A61B 18/1492; A61B 2017/00022; A61B 5/0031; A61B 17/12122; A61B 2018/00351; A61B 5/686; A61B 2017/00411; A61B 2560/0219; A61B 5/026; A61B 5/6869; A61B 5/14542; A61B 2560/0406; A61B 5/024; A61B 5/029; A61B 5/6862; A61M 27/002; A61M 2210/125; A61M 60/165; A61M 60/876; A61M 2205/3331; A61M 2205/3303; A61M 2205/04; A61M 2205/8206; A61M 2205/8243; A61M 2205/33; A61F 2/2418; A61F 2/2442; A61F 2250/0002; A61F 2/07; A61F 2250/0069; A61F 2250/0001
See application file for complete search history.

(56) References Cited

U.S. PATENT DOCUMENTS

| | | | |
|---|---|---|---|
| 4,537,186 A * | 8/1985 | Verschoof ............... A61F 6/225 |
| | | | 128/831 |
| 4,601,309 A | 7/1986 | Chang |
| 4,662,355 A | 5/1987 | Pieronne et al. |
| 4,705,507 A | 11/1987 | Boyles |
| 4,836,204 A | 6/1989 | Landymore et al. |
| 4,932,421 A * | 6/1990 | Kaali ...................... A61F 6/144 |
| | | | 128/833 |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,312,341 A | 5/1994 | Turi |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,531,759 A | 7/1996 | Kensey et al. |
| 5,545,137 A | 8/1996 | Rudie et al. |
| 5,556,386 A | 9/1996 | Todd |
| 5,584,803 A | 12/1996 | Stevens et al. |
| 5,597,377 A | 1/1997 | Aldea |
| 5,645,559 A | 7/1997 | Hachtman et al. |
| 5,655,548 A | 8/1997 | Nelson et al. |
| 5,662,711 A | 9/1997 | Douglas |
| 5,702,412 A | 12/1997 | Popov et al. |
| 5,725,552 A | 3/1998 | Kotula et al. |
| 5,741,297 A | 4/1998 | Simon |
| 5,795,307 A | 8/1998 | Krueger |
| 5,810,836 A | 9/1998 | Hussein et al. |
| 5,814,089 A | 9/1998 | Stokes et al. |
| 5,824,071 A | 10/1998 | Nelson et al. |
| 5,916,193 A | 6/1999 | Stevens et al. |
| 5,941,850 A | 8/1999 | Shah et al. |
| 5,948,006 A | 9/1999 | Mann |
| 5,949,632 A | 9/1999 | Barreras et al. |

| | | | |
|---|---|---|---|
| 5,957,949 A | 9/1999 | Leonhardt et al. |
| 6,039,759 A | 3/2000 | Carpentier et al. |
| 6,066,163 A | 5/2000 | John |
| 6,067,474 A | 5/2000 | Schulman et al. |
| 6,077,298 A | 6/2000 | Tu et al. |
| 6,099,495 A | 8/2000 | Kinghorn et al. |
| 6,126,686 A | 10/2000 | Badylak et al. |
| 6,165,188 A | 12/2000 | Saadat et al. |
| 6,166,518 A | 12/2000 | Echarri et al. |
| 6,210,318 B1 | 4/2001 | Lederman |
| 6,217,541 B1 | 4/2001 | Yu |
| 6,240,316 B1 | 5/2001 | Richmond et al. |
| 6,242,762 B1 | 6/2001 | Brown et al. |
| 6,254,564 B1 | 7/2001 | Wilk et al. |
| 6,259,951 B1 | 7/2001 | Kuzma et al. |
| 6,260,552 B1 | 7/2001 | Mortier et al. |
| 6,270,526 B1 | 8/2001 | Cox |
| 6,277,078 B1 | 8/2001 | Porat et al. |
| 6,302,892 B1 | 10/2001 | Wilk |
| 6,328,699 B1 | 12/2001 | Eigler et al. |
| 6,344,022 B1 | 2/2002 | Jarvik |
| 6,354,991 B1 | 3/2002 | Gross et al. |
| 6,358,277 B1 | 3/2002 | Duran |
| 6,381,496 B1 | 4/2002 | Meadows et al. |
| 6,406,422 B1 | 6/2002 | Landesberg |
| 6,447,539 B1 | 9/2002 | Nelson et al. |
| 6,451,051 B2 | 9/2002 | Drasler et al. |
| 6,458,153 B1 | 10/2002 | Bailey et al. |
| 6,468,303 B1 | 10/2002 | Amplatz et al. |
| 6,478,776 B1 | 11/2002 | Rosenman et al. |
| 6,491,705 B2 | 12/2002 | Gifford, III et al. |
| 6,516,227 B1 | 2/2003 | Meadows et al. |
| 6,527,698 B1 | 3/2003 | Kung et al. |
| 6,544,208 B2 | 4/2003 | Ethier et al. |
| 6,562,066 B1 | 5/2003 | Martin |
| 6,572,652 B2 | 6/2003 | Shaknovich |
| 6,589,198 B1 | 7/2003 | Soltanpour et al. |
| 6,622,048 B1 | 9/2003 | Mann et al. |
| 6,632,169 B2 | 10/2003 | Korakianitis et al. |
| 6,638,303 B1 | 10/2003 | Campbell |
| 6,641,610 B2 | 11/2003 | Wolf et al. |
| 6,650,943 B1 | 11/2003 | Whitehurst et al. |
| 6,652,578 B2 | 11/2003 | Bailey et al. |
| 6,685,664 B2 | 2/2004 | Levin et al. |
| 6,712,836 B1 | 3/2004 | Berg et al. |
| 6,733,485 B1 | 5/2004 | Whitehurst et al. |
| 6,735,474 B1 | 5/2004 | Loeb et al. |
| 6,735,475 B1 | 5/2004 | Kuzma et al. |
| 6,782,292 B2 | 8/2004 | Whitehurst |
| 6,788,975 B1 | 9/2004 | Whitehurst et al. |
| 6,820,019 B1 | 11/2004 | Kelly et al. |
| 6,832,114 B1 | 12/2004 | Whitehurst et al. |
| 6,845,267 B2 | 1/2005 | Harrison et al. |
| 6,862,479 B1 | 3/2005 | Whitehurst et al. |
| 6,871,099 B1 | 3/2005 | Kuzma et al. |
| 6,885,895 B1 | 4/2005 | Whitehurst et al. |
| 6,911,043 B2 | 6/2005 | Myers et al. |
| 6,922,590 B1 | 7/2005 | Whitehurst |
| 6,937,891 B2 | 8/2005 | Rodriguez et al. |
| 6,950,706 B2 | 9/2005 | Jensen et al. |
| 6,950,707 B2 | 9/2005 | Whitehurst |
| 6,970,741 B1 | 11/2005 | Whitehurst et al. |
| 7,001,409 B2 | 2/2006 | Amplatz |
| 7,003,352 B1 | 2/2006 | Whitehurst |
| 7,011,095 B2 | 3/2006 | Wolf et al. |
| 7,013,177 B1 | 3/2006 | Meadows et al. |
| 7,024,246 B2 | 4/2006 | Acosta et al. |
| 7,054,689 B1 | 5/2006 | Whitehurst et al. |
| 7,054,691 B1 | 5/2006 | Kuzma et al. |
| 7,056,294 B2 | 6/2006 | Khairkhahan et al. |
| 7,070,577 B1 | 7/2006 | Haller et al. |
| 7,089,057 B2 | 8/2006 | Heathershaw et al. |
| 7,110,821 B1 | 9/2006 | Ross |
| 7,136,701 B2 | 11/2006 | Greatbatch et al. |
| 7,146,209 B2 | 12/2006 | Gross et al. |
| 7,149,587 B2 | 12/2006 | Wardle et al. |
| 7,149,773 B2 | 12/2006 | Haller et al. |
| 7,151,961 B1 | 12/2006 | Mcclure et al. |
| 7,155,279 B2 | 12/2006 | Whitehurst et al. |

(56) References Cited

U.S. PATENT DOCUMENTS

| | | | |
|---|---|---|---|
| 7,155,284 B1 | 12/2006 | Whitehurst et al. |
| 7,167,751 B1 | 1/2007 | Whitehurst et al. |
| 7,175,656 B2 | 2/2007 | Khairkhahan |
| 7,177,698 B2 | 2/2007 | Klosterman et al. |
| 7,203,548 B2 | 4/2007 | Bradley et al. |
| 7,254,449 B2 | 8/2007 | Karunasiri |
| 7,270,675 B2 | 9/2007 | Chun et al. |
| 7,292,890 B2 | 11/2007 | Bradley et al. |
| 7,294,115 B1 | 11/2007 | Wilk |
| 7,308,303 B2 | 12/2007 | Whitehurst et al. |
| 7,311,690 B2 | 12/2007 | Burnett |
| 7,311,730 B2 | 12/2007 | Gabbay |
| 7,317,947 B2 | 1/2008 | Wahlstrand et al. |
| 7,317,951 B2 | 1/2008 | Schneider et al. |
| 7,330,756 B2 | 2/2008 | Marnfeldt |
| 7,337,003 B2 | 2/2008 | Malinowski |
| 7,349,741 B2 | 3/2008 | Maltan et al. |
| 7,390,310 B2 | 6/2008 | McCusker et al. |
| 7,433,737 B2 | 10/2008 | He et al. |
| 7,437,193 B2 | 10/2008 | Parramon et al. |
| 7,444,180 B2 | 10/2008 | Kuzma et al. |
| 7,481,759 B2 | 1/2009 | Whitehurst et al. |
| 7,483,746 B2 | 1/2009 | Lee et al. |
| 7,483,748 B2 | 1/2009 | Torgerson et al. |
| 7,498,516 B1 | 3/2009 | He |
| 7,513,908 B2 | 4/2009 | Lattouf |
| 7,524,329 B2 | 4/2009 | Rucker |
| 7,524,330 B2 | 4/2009 | Berreklouw |
| 7,524,332 B2 | 4/2009 | Osborne et al. |
| 7,532,936 B2 | 5/2009 | Erickson et al. |
| 7,608,067 B2 | 10/2009 | Bonni |
| 7,610,100 B2 | 10/2009 | Jaax et al. |
| 7,617,001 B2 | 11/2009 | Penner et al. |
| 7,634,318 B2 | 12/2009 | Tran et al. |
| 7,672,732 B2 | 3/2010 | Sun et al. |
| 7,684,867 B2 | 3/2010 | Whitehurst et al. |
| 7,699,059 B2 | 4/2010 | Fonseca et al. |
| 7,706,892 B2 | 4/2010 | Haller et al. |
| 7,729,758 B2 | 6/2010 | Parramon et al. |
| 7,736,327 B2 | 6/2010 | Wilk et al. |
| 7,742,817 B2 | 6/2010 | Malinowski et al. |
| 7,761,165 B1 | 7/2010 | Haller et al. |
| 7,769,467 B1 | 8/2010 | Emadi et al. |
| 7,777,641 B2 | 8/2010 | Karunasiri et al. |
| 7,780,725 B2 | 8/2010 | Haug et al. |
| 7,783,359 B2 | 8/2010 | Meadows |
| 7,794,473 B2 | 9/2010 | Tessmer et al. |
| 7,801,602 B2 | 9/2010 | Mcclure et al. |
| 7,803,021 B1 | 9/2010 | Brase |
| 7,805,200 B2 | 9/2010 | Kast et al. |
| 7,805,202 B2 | 9/2010 | Kuzma et al. |
| 7,806,921 B2 | 10/2010 | Hoffman |
| 7,813,804 B1 | 10/2010 | Jaax |
| 7,818,060 B2 | 10/2010 | Torgerson |
| 7,835,803 B1 | 11/2010 | Malinowski et al. |
| 7,840,268 B2 | 11/2010 | Blischak et al. |
| 7,840,279 B2 | 11/2010 | He |
| 7,853,321 B2 | 12/2010 | Whitehurst et al. |
| 7,857,819 B2 | 12/2010 | Jaax et al. |
| 7,860,570 B2 | 12/2010 | Whitehurst et al. |
| 7,877,136 B1 | 1/2011 | Moffitt et al. |
| 7,892,246 B2 | 2/2011 | Akin et al. |
| 7,905,901 B2 | 3/2011 | Corcoran et al. |
| 7,922,764 B2 | 4/2011 | Gordy et al. |
| 7,938,840 B2 | 5/2011 | Golden et al. |
| 7,941,227 B2 | 5/2011 | Barker |
| 7,945,323 B2 | 5/2011 | Jaax et al. |
| 7,957,805 B2 | 6/2011 | He |
| 7,967,769 B2 | 6/2011 | Faul et al. |
| 7,974,706 B2 | 7/2011 | Moffitt et al. |
| 7,988,724 B2 | 8/2011 | Salahich et al. |
| 7,991,483 B1 | 8/2011 | Atanasoska et al. |
| 8,012,198 B2 | 9/2011 | Hill et al. |
| 8,016,877 B2 | 9/2011 | Seguin et al. |
| 8,019,443 B2 | 9/2011 | Schleicher et al. |
| 8,027,735 B1 | 9/2011 | Tziviskos et al. |
| 8,043,360 B2 | 10/2011 | McNamara et al. |
| 8,046,073 B1 | 10/2011 | Pianca |
| 8,060,209 B2 | 11/2011 | Digiore et al. |
| 8,070,708 B2 | 12/2011 | Rottenberg et al. |
| 8,086,307 B2 | 12/2011 | Virag et al. |
| 8,091,556 B2 | 1/2012 | Keren et al. |
| 8,096,959 B2 | 1/2012 | Stewart et al. |
| 8,099,168 B2 | 1/2012 | Roche |
| 8,145,314 B2 | 3/2012 | Mcdonald |
| 8,147,545 B2 | 4/2012 | Avior |
| 8,157,860 B2 | 4/2012 | McNamara et al. |
| 8,172,896 B2 | 5/2012 | McNamara et al. |
| 8,175,710 B2 | 5/2012 | He |
| 8,175,717 B2 | 5/2012 | Haller et al. |
| 8,192,418 B2 | 6/2012 | Robinson et al. |
| 8,209,017 B1 | 6/2012 | Mcdonald |
| 8,219,196 B2 | 7/2012 | Torgerson |
| 8,235,916 B2 | 8/2012 | Whiting et al. |
| 8,235,933 B2 | 8/2012 | Keren et al. |
| 8,244,367 B2 | 8/2012 | Wahlstrand et al. |
| 8,244,377 B1 | 8/2012 | Pianca et al. |
| 8,246,677 B2 | 8/2012 | Ryan |
| 8,252,042 B2 | 8/2012 | McNamara et al. |
| 8,260,412 B2 | 9/2012 | Krause et al. |
| 8,260,432 B2 | 9/2012 | Digiore et al. |
| 8,260,434 B2 | 9/2012 | Digiore et al. |
| 8,265,771 B2 | 9/2012 | Donofrio et al. |
| 8,271,089 B2 | 9/2012 | Dinsmoor et al. |
| 8,271,094 B1 | 9/2012 | Moffitt et al. |
| 8,280,500 B2 | 10/2012 | Chow |
| 8,285,388 B2 | 10/2012 | Wahlstrand |
| 8,290,599 B2 | 10/2012 | Walter et al. |
| 8,303,511 B2 | 11/2012 | Eigler et al. |
| 8,328,751 B2 | 12/2012 | Keren et al. |
| 8,332,049 B2 | 12/2012 | Pianca et al. |
| 8,335,570 B2 | 12/2012 | Mcdonald |
| 8,340,782 B2 | 12/2012 | Mcdonald et al. |
| 8,348,996 B2 | 1/2013 | Tuval et al. |
| 8,352,035 B2 | 1/2013 | Schleicher et al. |
| 8,352,039 B2 | 1/2013 | Davis et al. |
| 8,359,107 B2 | 1/2013 | Pianca et al. |
| 8,364,279 B2 | 1/2013 | Mcdonald et al. |
| 8,374,686 B2 | 2/2013 | Ghanem et al. |
| 8,380,324 B2 | 2/2013 | Mcdonald et al. |
| 8,380,325 B2 | 2/2013 | Mcdonald |
| 8,386,038 B2 | 2/2013 | Bianchi et al. |
| 8,398,708 B2 | 3/2013 | Meiri et al. |
| 8,401,214 B2 | 3/2013 | Perkins et al. |
| 8,401,654 B1 | 3/2013 | Foster et al. |
| 8,406,893 B2 | 3/2013 | Krause et al. |
| 8,406,897 B2 | 3/2013 | Mcdonald et al. |
| 8,412,332 B2 | 4/2013 | Massoud-Ansari et al. |
| 8,412,349 B2 | 4/2013 | Barker |
| 8,417,343 B2 | 4/2013 | Bolea et al. |
| 8,433,409 B2 | 4/2013 | Johnson et al. |
| 8,437,851 B2 | 5/2013 | Corbucci et al. |
| 8,442,649 B2 | 5/2013 | Mcdonald |
| 8,452,407 B2 | 5/2013 | Whitehurst et al. |
| 8,460,366 B2 | 6/2013 | Rowe |
| 8,460,372 B2 | 6/2013 | McNamara et al. |
| 8,478,423 B2 | 7/2013 | Mcdonald et al. |
| 8,494,654 B2 | 7/2013 | Pianca et al. |
| 8,506,514 B2 | 8/2013 | Pedersen et al. |
| 8,515,541 B1 | 8/2013 | Jaax et al. |
| 8,527,045 B2 | 9/2013 | Krause et al. |
| 8,531,153 B2 | 9/2013 | Baarman et al. |
| 8,538,538 B2 | 9/2013 | Torgerson et al. |
| 8,543,210 B2 | 9/2013 | Sharma |
| 8,548,582 B2 | 10/2013 | Mcdonald et al. |
| 8,597,225 B2 | 12/2013 | Kapadia |
| 8,600,507 B2 | 12/2013 | Brase et al. |
| 8,600,512 B2 | 12/2013 | Whitehurst et al. |
| 8,600,518 B2 | 12/2013 | Meadows et al. |
| 8,606,355 B1 | 12/2013 | Krause |
| 8,626,297 B2 | 1/2014 | Jaax et al. |
| 8,638,062 B2 | 1/2014 | Baarman et al. |
| 8,644,933 B2 | 2/2014 | Ozawa et al. |
| 8,647,381 B2 | 2/2014 | Essinger et al. |

(56)　　　　　References Cited

U.S. PATENT DOCUMENTS

| | | | |
|---|---|---|---|
| 8,655,451 B2 | 2/2014 | Klosterman et al. |
| 8,670,823 B2 | 3/2014 | Murtonen |
| 8,676,322 B2 | 3/2014 | Whitehurst et al. |
| 8,682,439 B2 | 3/2014 | Derohan et al. |
| 8,688,235 B1 | 4/2014 | Pianca et al. |
| 8,696,611 B2 | 4/2014 | Nitzan et al. |
| 8,712,542 B2 | 4/2014 | Mcmorrow et al. |
| 8,718,790 B2 | 5/2014 | Pianca |
| 8,740,962 B2 | 6/2014 | Finch et al. |
| 8,744,568 B2 | 6/2014 | Weber |
| 8,744,591 B2 | 6/2014 | Davis et al. |
| 8,745,845 B2 | 6/2014 | Finch et al. |
| 8,747,458 B2 | 6/2014 | Tuval et al. |
| 8,752,258 B2 | 6/2014 | Finch et al. |
| 8,755,881 B2 | 6/2014 | Kaiser et al. |
| 8,761,886 B2 | 6/2014 | Stancer et al. |
| 8,764,848 B2 | 7/2014 | Callaghan et al. |
| 8,768,488 B2 | 7/2014 | Barker |
| 8,774,941 B2 | 7/2014 | Pianca |
| 8,781,596 B2 | 7/2014 | Aghassian et al. |
| 8,792,994 B2 | 7/2014 | Venancio |
| 8,805,537 B1 | 8/2014 | Cong et al. |
| 8,812,107 B2 | 8/2014 | Virag et al. |
| 8,818,483 B2 | 8/2014 | Romero |
| 8,818,505 B2 | 8/2014 | Bhunia et al. |
| 8,818,508 B2 | 8/2014 | Scheiner |
| 8,845,705 B2 | 9/2014 | Perkins et al. |
| 8,849,396 B2 | 9/2014 | Derohan et al. |
| 8,849,414 B2 | 9/2014 | Lee |
| 8,849,419 B2 | 9/2014 | Lee |
| 8,849,422 B2 | 9/2014 | Pianca |
| 8,868,207 B2 | 10/2014 | Mcdonald et al. |
| 8,874,206 B2 | 10/2014 | Malinowski et al. |
| 8,882,697 B2 | 11/2014 | Celermajer et al. |
| 8,897,876 B2 | 11/2014 | Sundaramurthy et al. |
| 8,909,352 B2 | 12/2014 | Venook et al. |
| 8,909,354 B2 | 12/2014 | Orinski |
| 8,914,112 B2 | 12/2014 | Whitehurst et al. |
| 8,923,970 B2 | 12/2014 | Bar-yoseph et al. |
| 8,936,630 B2 | 1/2015 | Denison et al. |
| 8,942,935 B2 | 1/2015 | Michaels et al. |
| 8,951,223 B2 | 2/2015 | McNamara et al. |
| 8,965,511 B2 | 2/2015 | Greiner et al. |
| 8,965,528 B2 | 2/2015 | Howard |
| 8,979,758 B2 | 3/2015 | Stein et al. |
| 9,005,155 B2 | 4/2015 | Sugimoto |
| 9,008,778 B2 | 4/2015 | Gupta et al. |
| 9,020,589 B2 | 4/2015 | Torgerson |
| 9,034,034 B2 | 5/2015 | Nitzan et al. |
| 9,056,206 B2 | 6/2015 | Torgerson et al. |
| 9,065,284 B2 | 6/2015 | Malpas et al. |
| 9,072,447 B2 | 7/2015 | Chow |
| 9,079,039 B2 | 7/2015 | Carlson et al. |
| 9,095,701 B2 | 8/2015 | Govea et al. |
| 9,101,755 B2 | 8/2015 | Pianca |
| 9,119,967 B2 | 9/2015 | Gupta et al. |
| 9,119,970 B2 | 9/2015 | Va |
| 9,132,276 B2 | 9/2015 | Meskens |
| 9,138,213 B2 | 9/2015 | Amin et al. |
| 9,143,003 B2 | 9/2015 | Baarman et al. |
| 9,162,048 B2 | 10/2015 | Romero et al. |
| 9,162,055 B2 | 10/2015 | Pianca et al. |
| 9,180,291 B2 | 11/2015 | Leven |
| 9,180,303 B2 | 11/2015 | Goetz |
| 9,192,772 B1 | 11/2015 | Tsukamoto et al. |
| 9,205,236 B2 | 12/2015 | McNamara et al. |
| 9,205,251 B2 | 12/2015 | Govea et al. |
| 9,215,075 B1 | 12/2015 | Poltorak |
| 9,216,282 B1 | 12/2015 | Moffitt et al. |
| 9,216,563 B2 | 12/2015 | Barner |
| 9,232,997 B2 | 1/2016 | Sugimoto et al. |
| 9,259,571 B2 | 2/2016 | Straka et al. |
| 9,265,934 B2 | 2/2016 | Pianca et al. |
| 9,277,995 B2 | 3/2016 | Celermajer et al. |
| 9,283,378 B2 | 3/2016 | Govea |
| 9,289,592 B2 | 3/2016 | Chinn et al. |
| 9,289,600 B2 | 3/2016 | Govea et al. |
| 9,302,094 B2 | 4/2016 | Govea |
| 9,302,113 B2 | 4/2016 | Ranu et al. |
| 9,320,891 B2 | 4/2016 | Anderson et al. |
| 9,320,901 B2 | 4/2016 | Torgerson et al. |
| 9,339,657 B2 | 5/2016 | Stancer et al. |
| 9,345,897 B2 | 5/2016 | Dorman et al. |
| 9,352,145 B2 | 5/2016 | Whitehurst et al. |
| 9,358,371 B2 | 6/2016 | McNamara et al. |
| 9,364,658 B2 | 6/2016 | Wechter |
| 9,381,342 B2 | 7/2016 | Barker |
| 9,393,422 B2 | 7/2016 | Moffitt et al. |
| 9,399,131 B2 | 7/2016 | Digiore et al. |
| 9,402,993 B2 | 8/2016 | Howard et al. |
| 9,403,011 B2 | 8/2016 | Mercanzini |
| 9,409,032 B2 | 8/2016 | Brase et al. |
| 9,415,154 B2 | 8/2016 | Leven |
| 9,415,212 B2 | 8/2016 | Barker |
| 9,415,213 B2 | 8/2016 | Venook et al. |
| 9,440,066 B2 | 9/2016 | Black |
| 9,456,812 B2 | 10/2016 | Finch et al. |
| 9,492,655 B2 | 11/2016 | Pianca et al. |
| 9,498,635 B2 | 11/2016 | Dellamano et al. |
| 9,498,636 B2 | 11/2016 | Dellamano et al. |
| 9,504,839 B2 | 11/2016 | Leven |
| 9,504,842 B2 | 11/2016 | Guardiani et al. |
| 9,517,334 B2 | 12/2016 | Barner et al. |
| 9,533,141 B2 | 1/2017 | Black et al. |
| 9,537,344 B2 | 1/2017 | Thompson et al. |
| 9,539,432 B2 | 1/2017 | Dellamano et al. |
| 9,544,068 B2 | 1/2017 | Arbabian et al. |
| 9,560,980 B2 | 2/2017 | Charlton et al. |
| 9,561,362 B2 | 2/2017 | Malinowski |
| 9,597,505 B2 | 3/2017 | Donofrio et al. |
| 9,604,048 B2 | 3/2017 | Govea |
| 9,604,050 B2 | 3/2017 | Barker |
| 9,604,066 B2 | 3/2017 | Carbunaru et al. |
| 9,604,068 B2 | 3/2017 | Malinowski |
| 9,610,434 B2 | 4/2017 | Barker |
| 9,629,658 B2 | 4/2017 | Barker |
| 9,629,715 B2 | 4/2017 | Nitzan et al. |
| 9,642,993 B2 | 5/2017 | McNamara et al. |
| 9,643,010 B2 | 5/2017 | Ranu |
| 9,647,462 B2 | 5/2017 | Angst et al. |
| 9,649,480 B2 | 5/2017 | Sugimoto et al. |
| 9,649,489 B2 | 5/2017 | Wechter et al. |
| 9,655,528 B2 | 5/2017 | Zhu |
| 9,656,093 B2 | 5/2017 | Villarta et al. |
| 9,662,506 B2 | 5/2017 | Govea |
| 9,669,210 B2 | 6/2017 | Barker et al. |
| 9,681,948 B2 | 6/2017 | Levi et al. |
| 9,700,350 B2 | 7/2017 | Barker |
| 9,707,382 B2 | 7/2017 | Nitzan et al. |
| 9,707,406 B1 | 7/2017 | Dellamano et al. |
| 9,713,696 B2 | 7/2017 | Yacoby et al. |
| 9,713,725 B2 | 7/2017 | Bobgan et al. |
| 9,724,499 B2 | 8/2017 | Rottenberg et al. |
| 9,744,368 B2 | 8/2017 | Dinsmoor |
| 9,757,107 B2 | 9/2017 | McNamara et al. |
| 9,770,598 B2 | 9/2017 | Malinowski et al. |
| 9,775,636 B2 | 10/2017 | Fazio et al. |
| 9,775,987 B2 | 10/2017 | Donofrio et al. |
| 9,782,581 B2 | 10/2017 | Howard et al. |
| 9,782,582 B2 | 10/2017 | Govea et al. |
| 9,782,597 B2 | 10/2017 | Shanahan et al. |
| 9,808,613 B2 | 11/2017 | Mcdonald et al. |
| 9,814,881 B2 | 11/2017 | Moffitt |
| 9,826,963 B2 | 11/2017 | Scott et al. |
| 9,833,611 B2 | 12/2017 | Govea et al. |
| 9,833,615 B2 | 12/2017 | Pereira et al. |
| 9,833,622 B2 | 12/2017 | Moffitt et al. |
| 9,833,629 B2 | 12/2017 | Dellamano et al. |
| 9,839,788 B2 | 12/2017 | Dellamano et al. |
| 9,849,025 B2 | 12/2017 | Zaveri et al. |
| 9,867,981 B2 | 1/2018 | Black et al. |
| 9,878,148 B2 | 1/2018 | Leven et al. |
| 9,883,836 B2 | 2/2018 | Cahan et al. |
| 9,889,304 B2 | 2/2018 | Mercanzini |

(56) References Cited

U.S. PATENT DOCUMENTS

| | | | |
|---|---|---|---|
| 9,889,308 B2 | 2/2018 | Dellamano et al. |
| 9,901,737 B2 | 2/2018 | Moffitt et al. |
| 9,907,972 B2 | 3/2018 | Kameli |
| 9,918,856 B2 | 3/2018 | Favier et al. |
| 9,919,148 B2 | 3/2018 | Howard et al. |
| 9,925,377 B2 | 3/2018 | Moffitt et al. |
| 9,925,378 B2 | 3/2018 | Moffitt et al. |
| 9,931,109 B2 | 4/2018 | Burckhardt et al. |
| 9,937,036 B2 | 4/2018 | Sugimoto et al. |
| 9,943,670 B2 | 4/2018 | Keren et al. |
| 9,956,000 B2 | 5/2018 | Gardanier et al. |
| 9,956,394 B2 | 5/2018 | Howard et al. |
| 9,974,959 B2 | 5/2018 | Moffitt et al. |
| 9,980,815 B2 | 5/2018 | Nitzan et al. |
| 9,986,989 B2 | 6/2018 | Roche et al. |
| 9,987,482 B2 | 6/2018 | Nageri et al. |
| 9,987,493 B2 | 6/2018 | Torgerson et al. |
| 9,993,168 B2 | 6/2018 | Huang et al. |
| 10,022,054 B2 | 7/2018 | Najafi et al. |
| 10,022,542 B2 | 7/2018 | Yip et al. |
| 10,022,549 B2 | 7/2018 | Dellamano et al. |
| 10,027,179 B1 | 7/2018 | Bello et al. |
| 10,035,013 B2 | 7/2018 | Desalles et al. |
| 10,045,766 B2 | 8/2018 | McNamara et al. |
| 10,058,696 B2 | 8/2018 | Stouffer |
| 10,075,026 B2 | 9/2018 | Badr et al. |
| 10,076,403 B1 | 9/2018 | Eigler et al. |
| 10,076,408 B2 | 9/2018 | Basinger et al. |
| 10,117,580 B1 | 11/2018 | Puryear et al. |
| 10,117,740 B1 | 11/2018 | Lee |
| 10,122,222 B2 | 11/2018 | Hansen et al. |
| 10,130,806 B2 | 11/2018 | Leven et al. |
| 10,137,304 B2 | 11/2018 | Kallmyer |
| 10,147,248 B2 | 12/2018 | Graafstra |
| 10,173,055 B2 | 1/2019 | Howard et al. |
| 10,176,933 B2 | 1/2019 | Irazoqui et al. |
| 10,179,234 B2 | 1/2019 | Leven |
| 10,179,237 B2 | 1/2019 | Kane et al. |
| 10,188,375 B2 | 1/2019 | McNamara et al. |
| 10,201,686 B2 | 2/2019 | Saul et al. |
| 10,204,706 B2 | 2/2019 | Davis et al. |
| 10,207,087 B2 | 2/2019 | Keren |
| 10,226,616 B2 | 3/2019 | Barker |
| 10,232,169 B2 | 3/2019 | Govea et al. |
| 10,251,676 B2 | 4/2019 | Brunner et al. |
| 10,251,740 B2 | 4/2019 | Eigler et al. |
| 10,286,205 B2 | 5/2019 | Steinke et al. |
| 10,286,215 B2 | 5/2019 | Perkins et al. |
| 10,292,690 B2 | 5/2019 | Celermajer et al. |
| 10,307,602 B2 | 6/2019 | Leven |
| 10,335,607 B2 | 7/2019 | Orinski |
| 10,342,983 B2 | 7/2019 | Nageri et al. |
| 10,350,384 B2 | 7/2019 | Farnan et al. |
| 10,357,357 B2 | 7/2019 | Levi et al. |
| 10,368,981 B2 | 8/2019 | Nitzan et al. |
| 10,376,359 B2 | 8/2019 | Essinger et al. |
| 10,376,680 B2 | 8/2019 | McNamara et al. |
| 10,391,319 B2 | 8/2019 | Shuros et al. |
| 10,398,421 B2 | 9/2019 | Celermajer |
| 10,398,899 B2 | 9/2019 | Torgerson |
| 10,405,903 B1 | 9/2019 | Biesinger et al. |
| 10,413,284 B2 | 9/2019 | McNamara et al. |
| 10,413,286 B2 | 9/2019 | McNamara et al. |
| 10,413,737 B2 | 9/2019 | Bokil et al. |
| 10,413,739 B2 | 9/2019 | Funderburk |
| 10,426,968 B2 | 10/2019 | Casse et al. |
| 10,449,382 B2 | 10/2019 | Casse et al. |
| 10,463,305 B2 | 11/2019 | An et al. |
| 10,463,477 B2 | 11/2019 | Forcucci et al. |
| 10,463,490 B2 | 11/2019 | Rottenberg et al. |
| 10,478,594 B2 | 11/2019 | Yacoby et al. |
| 10,512,784 B2 | 12/2019 | Hahn et al. |
| 10,554,069 B2 | 2/2020 | Paralikar et al. |
| 10,568,751 B2 | 2/2020 | McNamara |
| 10,576,267 B2 | 3/2020 | Reddy et al. |
| 10,576,269 B2 | 3/2020 | Steinke et al. |
| 10,583,247 B2 | 3/2020 | Mandro |
| 10,588,611 B2 | 3/2020 | Magnin et al. |
| 10,603,485 B2 | 3/2020 | Nageri |
| 10,603,499 B2 | 3/2020 | Lopez |
| 10,603,505 B2 | 3/2020 | Casse et al. |
| 10,610,210 B2 | 4/2020 | Finch et al. |
| 10,610,694 B2 | 4/2020 | Reinke et al. |
| 10,624,621 B2 | 4/2020 | Celermajer |
| 10,625,072 B2 | 4/2020 | Serran |
| 10,632,292 B2 | 4/2020 | Forcucci et al. |
| 10,638,955 B2 | 5/2020 | Rowland et al. |
| 10,639,459 B2 | 5/2020 | Nitzan et al. |
| 10,639,486 B2 | 5/2020 | Linder et al. |
| 10,655,024 B2 | 5/2020 | Yadavalli et al. |
| 10,667,896 B2 | 6/2020 | Delaney, Jr. et al. |
| 10,667,904 B2 | 6/2020 | Marquez et al. |
| 10,668,294 B2 | 6/2020 | Koop et al. |
| 10,675,450 B2 | 6/2020 | Finch |
| 10,675,476 B2 | 6/2020 | Reddy et al. |
| 10,695,571 B2 | 6/2020 | Dellamano et al. |
| 10,709,886 B2 | 7/2020 | Nagaoka et al. |
| 10,709,888 B2 | 7/2020 | Pianca |
| 10,716,935 B2 | 7/2020 | Leven et al. |
| 10,751,542 B2 | 8/2020 | Demmer et al. |
| 10,772,557 B2 | 9/2020 | Windolf |
| 10,780,278 B2 | 9/2020 | Hahn et al. |
| 10,806,352 B2 | 10/2020 | Sweeney et al. |
| 10,813,744 B2 | 10/2020 | Gupta et al. |
| 10,820,987 B2 | 11/2020 | Basinger et al. |
| 10,821,286 B2 | 11/2020 | Acklin et al. |
| 10,828,151 B2 | 11/2020 | Nitzan et al. |
| 10,835,394 B2 | 11/2020 | Nae et al. |
| 10,835,757 B2 | 11/2020 | Register et al. |
| 10,849,522 B2 | 12/2020 | Eddy et al. |
| 10,856,767 B2 | 12/2020 | Dettmann et al. |
| 10,870,008 B2 | 12/2020 | Hahn et al. |
| 10,881,863 B2 | 1/2021 | Maile et al. |
| 10,881,869 B2 | 1/2021 | Maile et al. |
| 10,894,163 B2 | 1/2021 | Stahmann |
| 10,898,698 B1 | 1/2021 | Eigler et al. |
| 10,898,719 B2 | 1/2021 | Pivonka et al. |
| 10,910,863 B2 | 2/2021 | Otten |
| 10,912,645 B2 | 2/2021 | Rottenberg et al. |
| 10,918,476 B2 | 2/2021 | Otts |
| 10,918,873 B2 | 2/2021 | Funderburk |
| 10,918,875 B2 | 2/2021 | Maile et al. |
| 10,925,706 B2 | 2/2021 | Eigler et al. |
| 10,932,786 B2 | 3/2021 | McNamara et al. |
| 10,933,234 B2 | 3/2021 | Molnar et al. |
| 10,940,296 B2 | 3/2021 | Keren |
| 10,945,716 B2 | 3/2021 | Chen et al. |
| 10,960,214 B2 | 3/2021 | Steinke et al. |
| 10,967,192 B2 | 4/2021 | Lui et al. |
| 10,973,425 B2 | 4/2021 | Cao |
| 11,002,990 B2 | 5/2021 | Lee et al. |
| 11,020,592 B2 | 6/2021 | Tyulmankov et al. |
| 11,020,595 B2 | 6/2021 | Koop |
| 11,045,658 B2 | 6/2021 | Iyer et al. |
| 11,050,263 B2 | 6/2021 | Bae et al. |
| 11,052,259 B2 | 7/2021 | Stinauer et al. |
| 11,056,267 B2 | 7/2021 | Iyer et al. |
| 11,090,491 B2 | 8/2021 | Mishra et al. |
| 11,097,096 B2 | 8/2021 | Linden et al. |
| 11,116,988 B2 | 9/2021 | Maile et al. |
| 11,135,410 B2 | 10/2021 | Finch et al. |
| 11,135,439 B2 | 10/2021 | Deshazo et al. |
| 11,147,979 B2 | 10/2021 | Linder et al. |
| 11,160,980 B2 | 11/2021 | Mishra et al. |
| 11,160,984 B2 | 11/2021 | Deshazo et al. |
| 11,167,128 B2 | 11/2021 | Villarta |
| 11,172,959 B2 | 11/2021 | Leven |
| 11,198,006 B1 | 12/2021 | Nijlunsing et al. |
| 11,207,532 B2 | 12/2021 | Eddy et al. |
| 11,224,743 B2 | 1/2022 | Govea et al. |
| 11,241,166 B1 | 2/2022 | Lee |
| 11,241,576 B2 | 2/2022 | Hansen et al. |
| 11,253,685 B2 | 2/2022 | Fahey et al. |
| 11,291,846 B2 | 4/2022 | Chiang |

(56) References Cited

U.S. PATENT DOCUMENTS

| | | | |
|---|---|---|---|
| 11,311,373 | B2 | 4/2022 | Gutierrez et al. |
| 11,331,493 | B2 | 5/2022 | Pivonka et al. |
| 11,344,728 | B2 | 5/2022 | Mercanzini et al. |
| 11,357,992 | B2 | 6/2022 | Nageri et al. |
| 11,357,995 | B2 | 6/2022 | Dellamano et al. |
| 11,364,109 | B2 | 6/2022 | Basinger et al. |
| 11,369,267 | B2 | 6/2022 | Melodia et al. |
| 11,383,083 | B2 | 7/2022 | Bolea |
| 11,389,583 | B2 | 7/2022 | Noshadi |
| 11,400,291 | B2 | 8/2022 | Gnansia et al. |
| 11,426,595 | B2 | 8/2022 | Leven et al. |
| 11,458,309 | B2 | 10/2022 | Zorman et al. |
| 11,467,665 | B2 | 10/2022 | Gribetz |
| 11,493,556 | B2 | 11/2022 | Deshazo |
| 11,497,914 | B2 | 11/2022 | Hahn et al. |
| 11,504,526 | B2 | 11/2022 | Zhu |
| 11,511,121 | B2 | 11/2022 | Sit et al. |
| 11,524,174 | B2 | 12/2022 | Vansickle et al. |
| 11,529,510 | B2 | 12/2022 | Leven |
| 11,565,131 | B2 | 1/2023 | Vansickle et al. |
| 11,577,075 | B1 | 2/2023 | Gaudiani |
| 11,583,387 | B2 | 2/2023 | Boysset et al. |
| 11,607,163 | B2 | 3/2023 | Iyer et al. |
| 11,623,095 | B2 | 4/2023 | Esteller et al. |
| 11,642,065 | B2 | 5/2023 | Felix et al. |
| 11,679,263 | B2 | 6/2023 | Hsu et al. |
| 11,696,681 | B2 | 7/2023 | Felix et al. |
| 11,697,019 | B2 | 7/2023 | Mazanec |
| 11,701,019 | B2 | 7/2023 | Gunn et al. |
| 11,717,695 | B2 | 8/2023 | Keil |
| 11,737,667 | B2 | 8/2023 | Fink et al. |
| 11,737,896 | B2 | 8/2023 | Bhamra et al. |
| 11,745,023 | B2 | 9/2023 | Keil et al. |
| 11,791,657 | B2 | 10/2023 | Rotfogel et al. |
| 11,801,369 | B2 | 10/2023 | Fahey et al. |
| 11,806,547 | B2 | 11/2023 | Howard |
| 2002/0151770 | A1 | 10/2002 | Noll et al. |
| 2002/0169371 | A1 | 11/2002 | Gilderdale |
| 2002/0169475 | A1 | 11/2002 | Gainor et al. |
| 2002/0177891 | A1 | 11/2002 | Miles et al. |
| 2003/0125798 | A1 | 7/2003 | Martin |
| 2003/0127090 | A1 | 7/2003 | Gifford et al. |
| 2003/0204222 | A1 | 10/2003 | Leinders et al. |
| 2003/0208244 | A1 | 11/2003 | Stein et al. |
| 2004/0016514 | A1 | 1/2004 | Nien |
| 2004/0077988 | A1 | 4/2004 | Tweden et al. |
| 2004/0088045 | A1 | 5/2004 | Cox |
| 2004/0093075 | A1 | 5/2004 | Kuehne |
| 2004/0106954 | A1 | 6/2004 | Whitehurst et al. |
| 2004/0122477 | A1 | 6/2004 | Whitehurst et al. |
| 2004/0143294 | A1 | 7/2004 | Corcoran et al. |
| 2004/0147869 | A1 | 7/2004 | Wolf et al. |
| 2004/0158143 | A1 | 8/2004 | Flaherty et al. |
| 2004/0162514 | A1 | 8/2004 | Alferness et al. |
| 2004/0162590 | A1 | 8/2004 | Mcclure et al. |
| 2004/0210190 | A1 | 10/2004 | Kohler et al. |
| 2004/0215067 | A1 | 10/2004 | Stiger et al. |
| 2004/0215323 | A1 | 10/2004 | Stiger |
| 2005/0004641 | A1 | 1/2005 | Pappu |
| 2005/0027332 | A1 | 2/2005 | Avrahami et al. |
| 2005/0033351 | A1 | 2/2005 | Newton |
| 2005/0134452 | A1 | 6/2005 | Smith |
| 2005/0165344 | A1 | 7/2005 | Dobak, III |
| 2005/0192627 | A1 | 9/2005 | Whisenant et al. |
| 2005/0204811 | A1 | 9/2005 | Neff |
| 2006/0025857 | A1 | 2/2006 | Bergheim et al. |
| 2006/0111660 | A1 | 5/2006 | Wolf et al. |
| 2006/0167522 | A1 | 7/2006 | Malinowski |
| 2006/0241717 | A1 | 10/2006 | Mcgivern et al. |
| 2007/0010837 | A1 | 1/2007 | Tanaka |
| 2007/0010852 | A1 | 1/2007 | Blaeser et al. |
| 2007/0043435 | A1 | 2/2007 | Seguin et al. |
| 2007/0050030 | A1 | 3/2007 | Kim |
| 2007/0142872 | A1 | 6/2007 | Hackworth et al. |
| 2007/0150019 | A1 | 6/2007 | Youker et al. |
| 2007/0213813 | A1 | 9/2007 | Von Segesser et al. |
| 2007/0293904 | A1 | 12/2007 | Gelbart et al. |
| 2008/0027513 | A1 | 1/2008 | Carbunaru |
| 2008/0077184 | A1 | 3/2008 | Denker et al. |
| 2008/0081962 | A1 | 4/2008 | Miller et al. |
| 2008/0097276 | A1 | 4/2008 | Bertrand et al. |
| 2008/0119891 | A1 | 5/2008 | Miles et al. |
| 2008/0212261 | A1 | 9/2008 | Ajayan et al. |
| 2008/0262566 | A1 | 10/2008 | Jaax |
| 2008/0288019 | A1 | 11/2008 | Heller |
| 2009/0005756 | A1 | 1/2009 | Foster |
| 2009/0105782 | A1 | 4/2009 | Mickle et al. |
| 2009/0118779 | A1 | 5/2009 | Najafi et al. |
| 2009/0132009 | A1 | 5/2009 | Torgerson |
| 2009/0178682 | A1* | 7/2009 | Tal ............................ A61F 6/20 |
| | | | 128/831 |
| 2009/0204133 | A1 | 8/2009 | Melzer et al. |
| 2009/0243956 | A1 | 10/2009 | Keilman et al. |
| 2009/0248122 | A1 | 10/2009 | Pianca |
| 2009/0248124 | A1 | 10/2009 | Chinn et al. |
| 2009/0275996 | A1 | 11/2009 | Burnes et al. |
| 2009/0276040 | A1 | 11/2009 | Rowe et al. |
| 2010/0010565 | A1 | 1/2010 | Gelbart et al. |
| 2010/0023103 | A1 | 1/2010 | Elborno |
| 2010/0076366 | A1 | 3/2010 | Henderson, Sr. et al. |
| 2010/0076517 | A1 | 3/2010 | Imran |
| 2010/0076535 | A1 | 3/2010 | Pianca et al. |
| 2010/0106028 | A1 | 4/2010 | Penner et al. |
| 2010/0114195 | A1 | 5/2010 | Burnes et al. |
| 2010/0114235 | A1 | 5/2010 | Jiang et al. |
| 2010/0114244 | A1 | 5/2010 | Manda et al. |
| 2010/0198308 | A1 | 8/2010 | Zhou et al. |
| 2010/0241195 | A1 | 9/2010 | Meadows et al. |
| 2010/0256696 | A1 | 10/2010 | Schleicher et al. |
| 2010/0280568 | A1 | 11/2010 | Bulkes et al. |
| 2010/0331918 | A1 | 12/2010 | Digiore et al. |
| 2010/0331919 | A1 | 12/2010 | Baldwin et al. |
| 2011/0009736 | A1 | 1/2011 | Maltz et al. |
| 2011/0009933 | A1 | 1/2011 | Barker |
| 2011/0034970 | A1 | 2/2011 | Barker |
| 2011/0054515 | A1 | 3/2011 | Bridgeman et al. |
| 2011/0093042 | A1 | 4/2011 | Torgerson et al. |
| 2011/0106220 | A1 | 5/2011 | Degiorgio et al. |
| 2011/0218480 | A1 | 9/2011 | Rottenberg et al. |
| 2011/0218481 | A1 | 9/2011 | Rottenberg et al. |
| 2011/0218549 | A1 | 9/2011 | Barker |
| 2011/0224681 | A1 | 9/2011 | Mcdonald |
| 2011/0230829 | A1* | 9/2011 | Fitzgerald .............. A61B 17/12 |
| | | | 604/96.01 |
| 2011/0230893 | A1 | 9/2011 | Barker |
| 2011/0257723 | A1 | 10/2011 | McNamara |
| 2011/0295183 | A1 | 12/2011 | Finch et al. |
| 2011/0301479 | A1 | 12/2011 | Ghanem et al. |
| 2012/0041287 | A1 | 2/2012 | Goodall et al. |
| 2012/0046710 | A1 | 2/2012 | Digiore et al. |
| 2012/0078320 | A1 | 3/2012 | Schotzko et al. |
| 2012/0109243 | A1 | 5/2012 | Hettrick et al. |
| 2012/0109261 | A1 | 5/2012 | Stancer et al. |
| 2012/0123496 | A1 | 5/2012 | Schotzko et al. |
| 2012/0191153 | A1 | 7/2012 | Swerdlow et al. |
| 2012/0215295 | A1 | 8/2012 | Pianca |
| 2012/0235502 | A1 | 9/2012 | Kesler et al. |
| 2012/0253261 | A1 | 10/2012 | Poletto et al. |
| 2012/0283773 | A1 | 11/2012 | Van Tassel et al. |
| 2012/0290062 | A1 | 11/2012 | McNamara et al. |
| 2012/0316610 | A1 | 12/2012 | Pianca et al. |
| 2013/0178784 | A1 | 7/2013 | McNamara et al. |
| 2013/0190799 | A1 | 7/2013 | Clark |
| 2013/0197336 | A1 | 8/2013 | Flo et al. |
| 2013/0197607 | A1 | 8/2013 | Wilder et al. |
| 2013/0226266 | A1 | 8/2013 | Murtonen et al. |
| 2013/0245755 | A1* | 9/2013 | Fehr ........................ A61F 2/14 |
| | | | 623/6.22 |
| 2013/0282091 | A1 | 10/2013 | Leven |
| 2013/0293025 | A1 | 11/2013 | Xu et al. |
| 2013/0317587 | A1 | 11/2013 | Barker |
| 2014/0018885 | A1 | 1/2014 | Pianca |
| 2014/0028109 | A1 | 1/2014 | Simon et al. |
| 2014/0039586 | A1 | 2/2014 | Barker et al. |

(56)　　　　References Cited

U.S. PATENT DOCUMENTS

| | | |
|---|---|---|
| 2014/0081154 A1 | 3/2014 | Toth |
| 2014/0128795 A1 | 5/2014 | Karen et al. |
| 2014/0128796 A1 | 5/2014 | Keren et al. |
| 2014/0163449 A1 | 6/2014 | Rottenberg et al. |
| 2014/0172057 A1 | 6/2014 | Orinski |
| 2014/0180371 A1 | 6/2014 | Leven |
| 2014/0277054 A1 | 9/2014 | McNamara et al. |
| 2014/0324138 A1 | 10/2014 | Wentz et al. |
| 2014/0330256 A1 | 11/2014 | Hyde et al. |
| 2014/0343645 A1 | 11/2014 | Wechter |
| 2014/0343646 A1 | 11/2014 | Leven |
| 2015/0005856 A1 | 1/2015 | Pianca et al. |
| 2015/0005860 A1 | 1/2015 | Howard et al. |
| 2015/0018913 A1 | 1/2015 | Leven |
| 2015/0018917 A1 | 1/2015 | Wechter et al. |
| 2015/0034217 A1 | 2/2015 | Vad |
| 2015/0045865 A1 | 2/2015 | Nageri et al. |
| 2015/0051677 A1 | 2/2015 | Marnfeldt |
| 2015/0051681 A1 | 2/2015 | Hershey |
| 2015/0075536 A1* | 3/2015 | Brenzel ................... A61F 6/225 |
| | | 128/831 |
| 2015/0084585 A1 | 3/2015 | Moran |
| 2015/0119796 A1 | 4/2015 | Finch |
| 2015/0200562 A1 | 7/2015 | Kilinc et al. |
| 2015/0230843 A1 | 8/2015 | Palmer et al. |
| 2015/0287544 A1 | 10/2015 | Irazoqui et al. |
| 2015/0335465 A1* | 11/2015 | Tal .......................... A61F 6/142 |
| | | 128/833 |
| 2015/0360037 A1 | 12/2015 | Hahn et al. |
| 2015/0360049 A1 | 12/2015 | Kaplitt et al. |
| 2015/0366612 A1* | 12/2015 | Crump ............... A61B 18/1815 |
| | | 606/33 |
| 2015/0374978 A1 | 12/2015 | Howard et al. |
| 2016/0022995 A1 | 1/2016 | Kothandaraman et al. |
| 2016/0023008 A1 | 1/2016 | Kothandaraman |
| 2016/0051828 A1 | 2/2016 | Stahler et al. |
| 2016/0082247 A1 | 3/2016 | Black et al. |
| 2016/0120550 A1* | 5/2016 | McNamara ........ A61B 17/0057 |
| | | 606/200 |
| 2016/0151179 A1 | 6/2016 | Favier et al. |
| 2016/0220357 A1 | 8/2016 | Anand et al. |
| 2016/0256693 A1 | 9/2016 | Parramon |
| 2016/0303301 A1 | 10/2016 | Bluvshtein et al. |
| 2016/0375237 A1 | 12/2016 | Hahn et al. |
| 2017/0000935 A1* | 1/2017 | Vasilyev ............. A61M 60/486 |
| 2017/0043077 A1 | 2/2017 | Tuseth et al. |
| 2017/0113026 A1 | 4/2017 | Finch |
| 2017/0143978 A1 | 5/2017 | Barker |
| 2017/0259078 A1 | 9/2017 | Howard |
| 2017/0281936 A1 | 10/2017 | Aghassian et al. |
| 2017/0326369 A1 | 11/2017 | Koop et al. |
| 2017/0326375 A1 | 11/2017 | Mcdonald et al. |
| 2017/0340460 A1 | 11/2017 | Rosen et al. |
| 2018/0014828 A1 | 1/2018 | Fonte et al. |
| 2018/0021569 A1 | 1/2018 | Pianca |
| 2018/0078773 A1 | 3/2018 | Thakur et al. |
| 2018/0247095 A1 | 8/2018 | Sundaram et al. |
| 2018/0250014 A1 | 9/2018 | Melanson et al. |
| 2018/0256865 A1 | 9/2018 | Finch et al. |
| 2018/0262037 A1 | 9/2018 | Meskeus |
| 2018/0369596 A1 | 12/2018 | Funderburk |
| 2018/0369606 A1 | 12/2018 | Zhang et al. |
| 2019/0019632 A1 | 1/2019 | Rusling et al. |
| 2019/0021597 A1 | 1/2019 | Nagy et al. |
| 2019/0021861 A1 | 1/2019 | Finch |
| 2019/0038895 A1 | 2/2019 | Pianca et al. |
| 2019/0070421 A1 | 3/2019 | Chen |
| 2019/0104936 A1 | 4/2019 | Gunn et al. |
| 2019/0105503 A1 | 4/2019 | Leven |
| 2019/0201695 A1 | 7/2019 | Hsu et al. |
| 2019/0209834 A1 | 7/2019 | Zhang et al. |
| 2019/0254814 A1 | 8/2019 | Nitzan et al. |
| 2019/0262118 A1 | 8/2019 | Eigler et al. |
| 2019/0269392 A1 | 9/2019 | Celermajer et al. |
| 2019/0269876 A1 | 9/2019 | Hsu et al. |
| 2019/0290924 A1 | 9/2019 | Funderburk |
| 2019/0328513 A1 | 10/2019 | Levi et al. |
| 2019/0336135 A1 | 11/2019 | Inouye et al. |
| 2019/0336163 A1 | 11/2019 | McNamara et al. |
| 2019/0343480 A1 | 11/2019 | Shute et al. |
| 2019/0350519 A1 | 11/2019 | Bailey et al. |
| 2020/0008870 A1 | 1/2020 | Gruba et al. |
| 2020/0009374 A1 | 1/2020 | Howard et al. |
| 2020/0023189 A1 | 1/2020 | Gribetz et al. |
| 2020/0060825 A1 | 2/2020 | Rottenberg et al. |
| 2020/0078175 A1* | 3/2020 | Axelrod ............... A61F 2/2487 |
| 2020/0078196 A1 | 3/2020 | Rosen et al. |
| 2020/0078558 A1 | 3/2020 | Yacoby et al. |
| 2020/0188143 A1 | 6/2020 | McNamara |
| 2020/0196943 A1 | 6/2020 | Minor et al. |
| 2020/0245991 A1 | 8/2020 | Celermajer |
| 2020/0253615 A1 | 8/2020 | Melanson et al. |
| 2020/0261705 A1 | 8/2020 | Nitzan et al. |
| 2020/0268515 A1 | 8/2020 | Vettukattil et al. |
| 2020/0269047 A1 | 8/2020 | Mazanec et al. |
| 2020/0315599 A1 | 10/2020 | Nae et al. |
| 2020/0330749 A1 | 10/2020 | Gribetz et al. |
| 2020/0368505 A1 | 11/2020 | Nae et al. |
| 2020/0376262 A1 | 12/2020 | Clark et al. |
| 2021/0007610 A1 | 1/2021 | Hendriks et al. |
| 2021/0008389 A1 | 1/2021 | Featherstone et al. |
| 2021/0023374 A1 | 1/2021 | Block et al. |
| 2021/0038230 A1 | 2/2021 | Larsen et al. |
| 2021/0046219 A1 | 2/2021 | Hendriks et al. |
| 2021/0052378 A1 | 2/2021 | Nitzan et al. |
| 2021/0059527 A1 | 3/2021 | Najafi |
| 2021/0100665 A1 | 4/2021 | Nae et al. |
| 2021/0106281 A1 | 4/2021 | Tran |
| 2021/0113382 A1* | 4/2021 | Soffer ................... A61M 31/00 |
| 2021/0121179 A1 | 4/2021 | Ben-david et al. |
| 2021/0121697 A1 | 4/2021 | Linde et al. |
| 2021/0153776 A1 | 5/2021 | Minar et al. |
| 2021/0177508 A1 | 6/2021 | Kellerman |
| 2021/0252251 A1 | 8/2021 | Subramanian |
| 2021/0257849 A1 | 8/2021 | Keil et al. |
| 2021/0259732 A1 | 8/2021 | Dicicco et al. |
| 2021/0259829 A1 | 8/2021 | Quinn |
| 2021/0259839 A1 | 8/2021 | Cole et al. |
| 2021/0275805 A1 | 9/2021 | Boor et al. |
| 2021/0288527 A1 | 9/2021 | Bae et al. |
| 2021/0290214 A1 | 9/2021 | Cole et al. |
| 2021/0298763 A1 | 9/2021 | Stahmann et al. |
| 2021/0299425 A1 | 9/2021 | Kume et al. |
| 2021/0299430 A1 | 9/2021 | Ratz et al. |
| 2021/0302751 A1 | 9/2021 | Brockman et al. |
| 2021/0353407 A1 | 11/2021 | Ma |
| 2021/0359550 A1 | 11/2021 | Budgett et al. |
| 2021/0361238 A1 | 11/2021 | Bak-Boychuk et al. |
| 2021/0361257 A1 | 11/2021 | Eimer et al. |
| 2021/0361948 A1 | 11/2021 | Leuthardt et al. |
| 2021/0370032 A1 | 12/2021 | Fahey et al. |
| 2021/0401418 A1 | 12/2021 | Dang et al. |
| 2022/0061679 A1 | 3/2022 | Adler et al. |
| 2022/0095992 A1 | 3/2022 | Guvenc et al. |
| 2022/0109402 A1 | 4/2022 | Gong et al. |
| 2022/0115187 A1 | 4/2022 | Kataky et al. |
| 2022/0117540 A1 | 4/2022 | Leuthardt et al. |
| 2022/0117555 A1 | 4/2022 | Zarbatauy et al. |
| 2022/0118228 A1 | 4/2022 | Fahey et al. |
| 2022/0118251 A1 | 4/2022 | Buddha et al. |
| 2022/0131424 A1 | 4/2022 | Charthad et al. |
| 2022/0141663 A1 | 5/2022 | Kothandaraman et al. |
| 2022/0151618 A1 | 5/2022 | Eigler et al. |
| 2022/0160309 A1 | 5/2022 | Poltorak |
| 2022/0167861 A1 | 6/2022 | Stahmann |
| 2022/0167921 A1 | 6/2022 | Aljuri et al. |
| 2022/0167922 A1 | 6/2022 | Gross et al. |
| 2022/0176120 A1 | 6/2022 | Kulkarni et al. |
| 2022/0176133 A1 | 6/2022 | Buddha et al. |
| 2022/0192677 A1 | 6/2022 | Wedul et al. |
| 2022/0192819 A1 | 6/2022 | Rodeheaver et al. |
| 2022/0202505 A1 | 6/2022 | Roche |
| 2022/0218355 A1 | 7/2022 | Wedul et al. |
| 2022/0218964 A1 | 7/2022 | Fahey et al. |

(56) References Cited

U.S. PATENT DOCUMENTS

| | | | |
|---|---|---|---|
| 2022/0226156 A1 | 7/2022 | Lee et al. | |
| 2022/0233872 A1 | 7/2022 | Perryman et al. | |
| 2022/0240856 A1 | 8/2022 | Stahmann et al. | |
| 2022/0252849 A1 | 8/2022 | Lee et al. | |
| 2022/0265157 A1 | 8/2022 | Charthad et al. | |
| 2022/0265280 A1* | 8/2022 | Chamorro | A61B 17/12172 |
| 2022/0266000 A1 | 8/2022 | Moffitt | |
| 2022/0288401 A1 | 9/2022 | Landherr et al. | |
| 2022/0300434 A1 | 9/2022 | Esteller | |
| 2022/0323781 A1 | 10/2022 | Subramanian et al. | |
| 2022/0339448 A1 | 10/2022 | Jayakumar et al. | |
| 2022/0354429 A1* | 11/2022 | Windheuser | A61F 2/90 |
| 2022/0362560 A1 | 11/2022 | Feldman | |
| 2022/0378303 A1 | 12/2022 | Melodia et al. | |
| 2022/0387785 A1 | 12/2022 | Huynh et al. | |
| 2022/0387799 A1 | 12/2022 | Feldman et al. | |
| 2022/0387806 A1 | 12/2022 | Mccormick et al. | |
| 2022/0407360 A1 | 12/2022 | Chiao et al. | |
| 2022/0413612 A1 | 12/2022 | Gribetz | |
| 2023/0010306 A1 | 1/2023 | Bashirullah et al. | |
| 2023/0041857 A1 | 2/2023 | Prutchi | |
| 2023/0056111 A1 | 2/2023 | Gururaj et al. | |
| 2023/0062862 A1 | 3/2023 | Forsell | |
| 2023/0065828 A1 | 3/2023 | Forsell | |
| 2023/0067764 A1 | 3/2023 | Forsell | |
| 2023/0075205 A1 | 3/2023 | Moran et al. | |
| 2023/0084193 A1 | 3/2023 | Fahey et al. | |
| 2023/0158280 A1 | 5/2023 | Andriola et al. | |
| 2023/0181906 A1 | 6/2023 | Moore et al. | |
| 2023/0198274 A1 | 6/2023 | Aghaeepour et al. | |
| 2023/0201546 A1 | 6/2023 | Fahey et al. | |
| 2023/0210374 A1 | 7/2023 | Charthad et al. | |
| 2023/0211076 A1 | 7/2023 | Weber et al. | |
| 2023/0218180 A1 | 7/2023 | Mujeeb-u-rahman et al. | |
| 2023/0226344 A1 | 7/2023 | Richardson | |
| 2023/0233229 A1 | 7/2023 | Picard et al. | |
| 2023/0233849 A1 | 7/2023 | Gorski et al. | |
| 2023/0238835 A1 | 7/2023 | Bae et al. | |
| 2023/0264014 A1 | 8/2023 | Corey et al. | |
| 2023/0277854 A1 | 9/2023 | Gavia | |
| 2023/0329634 A1 | 10/2023 | Zaman | |
| 2023/0346538 A1 | 11/2023 | Adler et al. | |
| 2023/0355994 A1 | 11/2023 | Forsell | |
| 2023/0355995 A1 | 11/2023 | Forsell | |
| 2023/0364433 A1 | 11/2023 | Forsell | |
| 2023/0364434 A1 | 11/2023 | Forsell | |
| 2023/0371953 A1 | 11/2023 | Pantages et al. | |
| 2023/0372683 A1 | 11/2023 | Andriola et al. | |
| 2023/0414177 A1* | 12/2023 | Valdez | A61B 5/6882 |
| 2024/0335643 A1 | 10/2024 | Andriola et al. | |
| 2024/0348482 A1 | 10/2024 | Charthad et al. | |

FOREIGN PATENT DOCUMENTS

| | | |
|---|---|---|
| AU | 2011332324 | 6/2013 |
| AU | 2012214279 | 8/2013 |
| AU | 2018228451 | 9/2019 |
| CA | 2785041 | 8/2011 |
| CA | 2786575 | 8/2011 |
| CA | 2818417 | 5/2012 |
| CA | 2955389 | 1/2016 |
| CA | 3054891 | 9/2018 |
| CN | 101415452 | 4/2009 |
| CN | 102458316 | 5/2012 |
| CN | 102905626 | 1/2013 |
| CN | 103458832 | 12/2013 |
| CN | 105662653 | 6/2016 |
| CN | 109646063 A | 4/2019 |
| CN | 110536657 | 12/2019 |
| EP | 1583585 | 10/2005 |
| EP | 2022532 | 2/2009 |
| EP | 2082708 | 7/2009 |
| EP | 2097012 | 9/2009 |
| EP | 2277586 | 1/2011 |
| EP | 2528646 | 12/2012 |
| EP | 2630811 | 8/2013 |
| EP | 2642954 | 10/2013 |
| EP | 2967867 | 1/2016 |
| EP | 3087953 | 11/2016 |
| EP | 3185948 | 7/2017 |
| EP | 3291773 | 3/2018 |
| EP | 3329862 | 6/2018 |
| EP | 3347085 | 7/2018 |
| EP | 3400053 | 11/2018 |
| EP | 3474777 | 5/2019 |
| EP | 3487385 | 5/2019 |
| EP | 3520706 | 8/2019 |
| EP | 3551897 | 9/2019 |
| EP | 3541472 | 9/2019 |
| EP | 3579907 | 12/2019 |
| EP | 3589238 | 1/2020 |
| EP | 3624701 | 3/2020 |
| EP | 2999412 | 5/2020 |
| EP | 3692949 | 8/2020 |
| EP | 3704780 | 9/2020 |
| EP | 3705154 | 9/2020 |
| EP | 3716877 | 10/2020 |
| EP | 3723586 | 10/2020 |
| EP | 3740163 | 11/2020 |
| EP | 3766431 | 1/2021 |
| EP | 3777657 | 2/2021 |
| EP | 3777961 | 2/2021 |
| EP | 3813933 | 5/2021 |
| EP | 3834737 | 6/2021 |
| EP | 3843618 | 7/2021 |
| EP | 3871626 | 9/2021 |
| EP | 3886761 | 10/2021 |
| EP | 3893731 | 10/2021 |
| EP | 3897369 | 10/2021 |
| EP | 3912676 | 11/2021 |
| EP | 3997776 | 5/2022 |
| EP | 4114514 | 1/2023 |
| EP | 4138981 | 3/2023 |
| EP | 4204076 | 7/2023 |
| EP | 4228733 | 8/2023 |
| EP | 4243925 | 9/2023 |
| EP | 4252263 | 10/2023 |
| IL | 176973 | 12/2006 |
| IL | 221127 | 9/2012 |
| IL | 226374 | 7/2013 |
| IL | 215975 | 11/2016 |
| IL | 227756 | 6/2017 |
| IL | 220201 | 8/2017 |
| IL | 253648 | 9/2017 |
| IL | 255379 | 12/2017 |
| IL | 252395 | 4/2020 |
| IN | 2011KN04472 | 7/2012 |
| IN | 2012KN01275 | 2/2013 |
| IN | 2013KN01954 | 11/2013 |
| IN | 2013CN06525 | 8/2014 |
| IN | 2012KN01988 | 8/2016 |
| JP | 2007527742 | 10/2007 |
| JP | 2010508093 | 3/2010 |
| JP | 2013046784 | 3/2013 |
| JP | 2014503246 | 2/2014 |
| JP | 2014512869 | 5/2014 |
| JP | 2020509812 | 4/2020 |
| KR | 20010046155 | 6/2001 |
| WO | WO2005002467 | 1/2005 |
| WO | WO2005074367 | 8/2005 |
| WO | WO2007083288 | 7/2007 |
| WO | WO2008055301 | 5/2008 |
| WO | WO2008089726 | 7/2008 |
| WO | WO2010000026 | 1/2010 |
| WO | WO2010128501 | 11/2010 |
| WO | WO2010129089 | 11/2010 |
| WO | WO2011093941 | 8/2011 |
| WO | WO2011094521 | 8/2011 |
| WO | WO2012071075 | 5/2012 |
| WO | WO2012085913 | 6/2012 |
| WO | WO2012109557 | 8/2012 |
| WO | WO2013014539 | 1/2013 |
| WO | WO2013096965 | 6/2013 |
| WO | WO2014091222 | 6/2014 |

(56) References Cited

FOREIGN PATENT DOCUMENTS

| WO | WO2014150106 | 9/2014 |
| WO | WO2014188279 | 11/2014 |
| WO | WO2016014821 | 1/2016 |
| WO | WO2016038115 | 3/2016 |
| WO | WO2016178171 | 11/2016 |
| WO | WO2017136767 | 8/2017 |
| WO | WO2017139606 | 8/2017 |
| WO | WO2017207981 | 12/2017 |
| WO | WO2017214740 | 12/2017 |
| WO | WO2018024868 | 2/2018 |
| WO | WO2018154138 | 8/2018 |
| WO | WO2018158747 | 9/2018 |
| WO | WO2019025785 | 2/2019 |
| WO | WO2019142152 | 7/2019 |
| WO | WO2019179447 | 9/2019 |
| WO | WO2019183078 | 9/2019 |
| WO | WO2019188917 | 10/2019 |
| WO | WO2019189079 | 10/2019 |
| WO | WO2019209420 | 10/2019 |
| WO | WO2020094085 | 5/2020 |
| WO | WO2020094087 | 5/2020 |
| WO | WO2020094094 | 5/2020 |
| WO | WO2020110048 | 6/2020 |
| WO | WO2020142613 | 7/2020 |
| WO | WO2020202046 | 10/2020 |
| WO | WO2020215090 | 10/2020 |
| WO | WO2020217194 | 10/2020 |
| WO | WO2020219265 | 10/2020 |
| WO | WO2020225698 | 11/2020 |
| WO | WO2020225757 | 11/2020 |
| WO | WO2020229636 | 11/2020 |
| WO | WO2020234751 | 11/2020 |
| WO | WO2020251700 | 12/2020 |
| WO | WO2020259492 | 12/2020 |
| WO | WO2021025905 | 2/2021 |
| WO | WO2021026485 | 2/2021 |
| WO | WO2021046753 | 3/2021 |
| WO | WO2021055264 | 3/2021 |
| WO | WO2021061272 | 4/2021 |
| WO | WO2021065873 | 4/2021 |
| WO | WO2021065874 | 4/2021 |
| WO | WO2021065875 | 4/2021 |
| WO | WO2021065912 | 4/2021 |
| WO | WO2021086707 | 5/2021 |
| WO | WO2021091566 | 5/2021 |
| WO | WO2021096766 | 5/2021 |
| WO | WO2021101707 | 5/2021 |
| WO | WO2021113670 | 6/2021 |
| WO | WO2021136252 | 7/2021 |
| WO | WO2021136261 | 7/2021 |
| WO | WO2021138041 | 7/2021 |
| WO | WO2021146342 | 7/2021 |
| WO | WO2021158559 | 8/2021 |
| WO | WO2021162888 | 8/2021 |
| WO | WO2021178636 | 9/2021 |
| WO | WO2021190547 | 9/2021 |
| WO | WO2021212011 | 10/2021 |
| WO | WO2021217059 | 10/2021 |
| WO | WO2021224736 | 11/2021 |
| WO | WO2021252397 | 12/2021 |
| WO | WO2022043555 | 3/2022 |
| WO | WO2022165320 | 8/2022 |
| WO | WO2022197748 | 9/2022 |
| WO | WO2022261492 | 12/2022 |
| WO | WO2022269278 | 12/2022 |
| WO | WO2022272131 | 12/2022 |
| WO | WO2023278612 | 1/2023 |
| WO | WO2023278725 | 1/2023 |
| WO | WO2023280858 | 1/2023 |
| WO | WO2023026124 | 3/2023 |
| WO | WO2023028164 | 3/2023 |
| WO | WO2023031039 | 3/2023 |
| WO | WO2023097337 | 6/2023 |
| WO | WO2023141266 | 7/2023 |
| WO | WO2023156529 | 8/2023 |
| WO | WO2023177690 | 9/2023 |
| WO | WO2023183417 | 9/2023 |

OTHER PUBLICATIONS

Abidin et al., "Design of Interdigital Structured Supercapacitor for Powering Biomedical Devices," 2011 IEEE Regional Symposium on Micro and Nano Electronics, pp. 88-91, Sep. 28-30, 2011, 4 pages.

Abidin et al., "Interdigitated MEMS Supercapacitor for Powering Heart Pacemaker," InTech, Nov. 2, 2016, 21 pages.

Aqueveque et al., "Wireless power system for charge supercapacitors as power sources for implantable devices," 2015 IEEE PELS Workshop on Emerging Technologies: Wireless Power (2015 WoW), Daejeon, South Korea, pp. 1-5, Jun. 5, 2015, 5 pages.

Baker, "New Mesh Technology Helps Holds Down Infection Rates In Pacemakers," KERA News, Jul. 29, 2019, 3 pages.

Chae et al., "A durable high-energy implantable energy storage system with binder-free electrodes useable in body fluids," Journal of Materials Chemistry A, Feb. 1, 2022, 11 pages.

Chae et al., "Electrode materials for biomedical patchable and implantable energy storage devices," Energy Storage Materials, vol. 24, pp. 113-128, Apr. 24, 2019, 16 pages.

Chen et al., "Stretchable Supercapacitors as Emergent Energy Storage Units for Health Monitoring Bioelectronics," Advanced Healthcare Materials, Dec. 10, 2019, 27 pages.

DeLong et al., "Wireless Energy Harvesting for Medical Applications," 2015 IEEE International Symposium on Antennas and Propagation & USNC/URSI National Radio Science Meeting, Vancouver, BC, Canada, Jul. 19-24, 2015, 1 page.

Fadhel et al., "Resonant Inductive Coupling for Wirelessly Powering Active Implants: Current Issues, Proposed Solutions and Future Technological attempts," Advanced Systems for Biomedical Application, Smart Sensors, Measurement and Instrumentation, vol. 39, Jul. 20, 2021, 37 pages.

Gall et al., "A Batteryless Energy Harvesting Storage System for Implantable Medical Devices Demonstrated In Situ," Circuits, Systems, and Signal Processing, Aug. 11, 2018, 14 pages.

Guida et al., "A 700 KHz Ultrasonic Link for Wireless Powering of Implantable Medical Devices," 2016 IEEE Sensors Conference, Oct. 30, 2016, 3 pages.

Guida et al., "Ultrasonically Rechargeable Platforms for Closed-Loop Distributed Sensing and Actuation in the Human Body," 2018 IEEE 19th International Workshop on Signal Processing Advances in Wireless Communications (SPAWC), Kalamata, Greece, 2018, pp. 1-5, Jun. 25-28, 2018, 5 pages.

He et al., "Biocompatible carbon nanotube fibers for implantable supercapacitors," Carbon, vol. 122, pp. 162-167, Oct. 2017, 6 pages.

Hu et al., "Wireless Power Supply for ICP Devices With Hybrid Supercapacitor and Battery Storage," IEEE Journal of Emerging and Selected Topics in Power Electronics, vol. 4, No. 1, pp. 273-279, Mar. 2016, 7 pages.

Kassanos et al., "Power and data communication in wearable and implantable devices," Wearable Sensors (Second Edition), pp. 279-309, Jan. 1, 2021, 31 pages.

Kim et al., "New and Emerging Energy Sources for Implantable Wireless Microdevices," IEEE Access, vol. 3, pp. 89-98, Feb. 23, 2015, 10 pages.

Lamberti et al., "TiO2 nanotube array as biocompatible electrode in view of implantable supercapacitors," Journal of Energy Storage, vol. 8, pp. 193-197, Aug. 27, 2016, 5 pages.

Lv et al., "A Degradable and Biocompatible Supercapacitor Implant Based on Functional Sericin Hydrogel Electrode," Advanced Materials Technologies, Mar. 2, 2023, 10 pages.

Mahesh et al., "Design Analysis of Defibrillator and Implementing Wireless Charging System," 2020 5th International Conference on Communication and Electronics Systems (ICCES), pp. 295-299, Jun. 10-12, 2020, 5 pages.

Mendoza-Ponce et al., "Super-capacitors for implantable medical devices with wireless power transmission," 2018 14th Conference

(56) References Cited

OTHER PUBLICATIONS on Ph.D. Research in Microelectronics and Electronics (PRIME), Prague, Czech Republic, 2018, pp. 241-244, Jul. 2-5, 2018, 4 pages.

Meng et al., "A flexible super-capacitive solid-state power supply for miniature implantable medical devices," Biomed Microdevices, Jul. 9, 2013, 11 pages.

Meng et al., "Ultrasmall Integrated 3D Micro-Supercapacitors Solve Energy Storage for Miniature Devices," Advanced Energy Materials, Dec. 12, 2013, 7 pages.

Monti et al., "Resonant Inductive Link for Remote Powering of Pacemakers," IEEE Transactions on Microwave Theory and Techniques, vol. 63, No. 11, pp. 3814-3822, Nov. 2015, 9 pages.

Mosa et al., "Ultrathin Graphene-Protein Supercapacitors for Miniaturized Bioelectronics," Advanced Energy Materials, Sep. 6, 2017, 21 pages.

Pandey et al., "Integration of Supercapacitors into Wirelessly Charged Biomedical Sensors," 2011 6th IEEE Conference on Industrial Electronics and Applications, Beijing, China, Jun. 21-23, 2011, pp. 56-61, 6 pages.

Park et al., "An implantable anti-biofouling biosupercapacitor with high energy performance," Biosensors and Bioelectronics, May 30, 2023, 16 pages.

Rabin et al., "Operability of Implantable Integrated Implants' Wireless Charging Device and Biotelemetric System," 2019 25th Conference of Open Innovations Association (FRUCT), Helsinki, Finland, 2019, pp. 257-264, Nov. 5-8, 2019, 8 pages.

Rita et al., "Effect of Supercapacitor on Power Supply for Rechargeable Implanted Medical Devices," Recent Innovations in Computing, ICRIC 2020, Lecture Notes in Electrical Engineering, vol. 701, pp. 123-134, Springer Nature Singapore Pte Ltd., Jan. 13, 2021, 12 pages.

Sanchez et al., "An Energy Management IC for Bio-Implants Using Ultracapacitors for Energy Storage," 2010 Symposium on VLSI Circuits, Jun. 15-17, 2010, 2 pages.

Sheng et al., "A soft implantable energy supply system that integrates wireless charging and biodegradable Zn-ion hybrid supercapacitors," Science Advances, Nov. 15, 2023, 17 pages.

Sheng et al., "A thin, deformable, high-performance supercapacitor implant that can be biodegraded and bioabsorbed within an animal body," Science Advances, Jan. 8, 2021, 11 pages.

Sheng et al., "Recent Advances of Energy Solutions for Implantable Bioelectronics," Advanced Healthcare Materials, Apr. 30, 2021, 25 pages.

Sim et al., "Biomolecule based fiber supercapacitor for implantable device," Nano Energy, vol. 47, pp. 385-392, May 2018, 8 pages.

Skunik-Nuckowska et al., "Integration of supercapacitors with enzymatic biobatteries toward more effective pulse-powered use in small-scale energy harvesting devices," Journal of Applied Electrochemistry, vol. 44, pp. 497-507, Jan. 4, 2014, 11 pages.

Su et al., "Stretchable Transparent Supercapacitors for Wearable and Implantable Medical Devices," Advanced Materials Technologies, Sep. 23, 2021, 6 pages.

Tian et al., "Implantable and Biodegradable Micro-Supercapacitor Based on a Superassembled Three-Dimensional Network Zn@PPy Hybrid Electrode," ACS Applied Materials Interfaces, Feb. 14, 2021, 10 pages.

Tran et al., "A compact wireless power transfer system at 915 MHz with supercapacitor for optogenetics applications," Sensors and Actuators A: Physical, Nov. 20, 2018, 9 pages.

Ungureanu et al., "Using of ISM radio bands for wireless charging of medical implants," 9th International Conference on Microelectronics and Computer Science, Chisinau, Republic of Moldova, Oct. 19-21, 2017, 4 pages.

Vanderbilt Heart and Vascular Institute, "Envelope' reduces cardiac implant infections," VUMC Reporter, Aug. 8, 2013, retrieved from website <URL: http://news.vanderbilt.edu/2013/08/envelop-reduces-cardiac-implant-infections/resorbablecardiac-implant>, 2 pages.

Wu et al., "Subcutaneous Solar Energy Harvesting for Self-Powered Wireless Implantable Sensor Systems," 2018 40th Annual International Conference of the IEEE Engineering in Medicine and Biology Society (EMBC), Honolulu, HI, USA, pp. 4657-4660, Jul. 18-21, 2018, 4 pages.

Xu et al., "Minimally invasive power sources for implantable electronics," Exploration, Jun. 8, 2023, 20 pages.

Extended European Search Report received for Application No. 21793483.5, Applicant: Shifamed Holdings, LLC; Date of Mailing: Apr. 18, 2024; 11 pages.

Jodi Perkins, "Corvia Medical and physiQ Partner in Global Phase 3 Heart Failure Clinical Trial to Leverage Novel Digital Endpoints," Press Release, 2019 Copyright, Medical Alley Association, 3 pages.

Lehner et al., "The Creation of an Interatrial Right-To-Left Shunt in Patients with Severe, Irreversible Pulmonary Hypertension: Rationale, Devices, Outcomes," Current Cardiology Reports (2019) 21: 31, https://doi.org/10.1007/s11886-019-1118-8; 9 pages.

International Search Report and Written Opinion received for International Application No. PCT/US20/063360 filed Dec. 4, 2020; Applicant: Shifamed Holdings, LLC; Date of Mailing: Apr. 5, 2021; 13 pages.

International Search Report and Written Opinion received for International Application No. PCT/US20/12059, filed Jan. 2, 2020; Applicant: Shifamed Holdings, LLC; Date of Mailing: Jun. 5, 2020; 12 pages.

International Search Report and Written Opinion received for International Application No. PCT/US21/28931, filed Apr. 23, 2021; Applicant: Shifamed Holdings, LLC; Date of Mailing: Sep. 24, 2021; 20 pages.

International Search Report and Written Opinion received for International Application No. PCT/US22/35764, filed Jun. 30, 2022; Applicant: Shifamed Holdings, LLC; Date of Mailing: Sep. 19, 2022; 10 pages.

International Search Report and Written Opinion received for International Application No. PCT/US22/34995, filed Jun. 24, 2022; Applicant: Shifamed Holdings, LLC; Date of Mailing: Nov. 18, 2022; 17 pages.

Perk et al., "Catheter-based left atrial appendage occlusion procedure: role of echocardiography," published on behalf of the European Society of Cardiology, Sep. 8, 2011, 7 pages.

Collado et al, "Left Atrial Appendage Occlusion for Stroke Prevention in Nonvalvular Atrial Fibrillation," Journal of the American Heart Association, Jun. 2021, 18 pages.

Ando et al., "Left ventricular decompression through a patent foramen ovale in a patient with hypertrophic cardiomyopathy: a case report," Cardiovascular Ultrasound volume, Article No. 2 (2004).

Braunwald, Heart Disease, Chapter 6, 2015, p. 186.

Bridges et al., "The Society of Thoracic Surgeons practice guideline series: transmyocardial laser revascularization," The Annals of Thoracic Surgery, vol. 77, Issue 4, Apr. 2004, pp. 1494-1502.

Bristow et al., "Improvement in cardiac myocyte function by biological effects of medical therapy: A new concept in the treatment of heart failure," European Heart Journal, vol. 16, Issue suppl. F, Jul. 1995, pp. 20-31.

Case et al., "Relief of High Left-Atrial Pressure in Left-Ventricular Failure," Lancet, Oct. 17, 1964, pp. 841-842.

Coats et al., "Controlled trial of physical training in chronic heart failure. Exercise performance, hemodynamics, ventilation, and autonomic function," Circulation, 1992;85:2119-2131.

Davies et al., "Reduced contraction and altered frequency response of isolated ventricular myocytes from patients with heart failure," Circulation, (1995), 92:2540-2549, Circulation, (1995), 92:2540-2549.

Ennezat et al., "An unusual case of low-flow, low gradient severe aortic stenosis: Left-to-right shunt due to atrial septal defect," Cardiology, (2009), 113(2):146-148.

Ewert et al., "Masked Left Ventricular Restriction in Elderly Patients With Atrial Septal Defects: A Contraindication for Closure," Catheterization and Cardiovascular Interventions, 52: 177-180, 2001.

Ewert et al., "Acute left heart failure after interventional occlusion of an atrial septal defect," Z. Kardiol., Catheterization and Cardiovascular Interventions, (May 2001), 90(5):362-366.

(56) References Cited

OTHER PUBLICATIONS

Geiran et al., "Changes in cardiac dynamics by opening an interventricular shunt in dogs," J. Surg. Res., (Jan. 1990), 48(1):6-12.

Gelernter-Yaniv et al., "Transcatheter closure of left-to-right interatrial shunts to resolve hypoxemia," Congenit. Heart Dis., (Jan. 2008), 31(1):47-53.

Gewillig et al., "Creation with a stent of an unrestrictive lasting atrial communication," Cardio. Young, (2002), 12(4):404-407.

Khositseth et al., "Transcatheter Amplatzer Device Closure of Atrial Septal Defect and Patent Foramen Ovale in Patients With Presumed Paradoxical Embolism," Mayo Clinic Proc., 79:35-41 (2004).

Kramer et al., "Controlled study of captopril in chronic heart failure: A rest and exercise hemodynamic study," Circulation, (1983), 67(4):807-816.

Lai et al., "Bidirectional shunt through a residual atrial septal defect after percutaneous transvenous mitral commissurotomy," Cardiology, (1993), 83(3):205-207.

Lemmer et al., "Surgical implications of atrial septal defect complicating aortic balloon valvuloplasty," Ann. thorac. Surg., (Aug. 1989), 48(2):295-297.

Park et al., "Blade atrial septostomy: collaborative study," Circulation, 66(2):258-266 (1982).

Roven et al., "Effect of Compromising Right Ventricular Function in Left Ventricular Failure by Means of Interatrial and Other Shunts," American Journal Cardiology, 24:209-219 (1969).

Salehian et al., "Improvements in Cardiac Form and Function After Transcatheter Closure of Secundum Atrial Septal Defects," Journal of the American College of Cardiology, 45(4):499-504 (2005).

Schmitto et al., "Chronic heart failure induced by multiple sequential coronary microembolization in sheep," The International Journal of Artificial Organs, 31(4):348-353 (2008).

Schubert et al., "Left ventricular conditioning in the elderly patient to prevent congestive heart failure after transcatheter closure of the atrial septal defect," Catheter Cardiovasc. Interv., (2005), 64(3):333-337.

Stormer et al., "Comparative study of in vitro flow characteristics between a human aortic valve and a designed aortic and six corresponding types of prosthetic heart valves," European Surgical Research, (1976), 8(2):117-131.

Stumper et al., "Modified technique of stent fenestration of the atrial septum, Heart," (2003), 89:1227-1230.

Trainor et al., "Comparative Pathology of an Implantable Left Atrial Pressure Sensor," ASAIO Journal, Clinical Cardiovascular/Cardiopulmonary Bypass, 59(5):486-92 (2013).

Zhou et al., "Unidirectional valve patch for repair of cardiac septal defects with pulmonary hypertension," Annals of Thoracic Surgeons, 60: 1245-1249, 1995.

* cited by examiner

ANTENNA ASSEMBLIES FOR MEDICAL SYSTEMS AND ASSOCIATED SYSTEMS AND METHODS

CROSS-REFERENCE TO RELATED APPLICATION(S)

This application is a continuation-in-part of International Patent Application No. PCT/US2022/034995, filed Jun. 24, 2022, which claims the benefit of U.S. Provisional Application No. 63/215,309, filed Jun. 25, 2021, both of which are incorporated herein by reference in their entireties.

TECHNICAL FIELD

The present technology generally relates to implantable medical devices and systems and, in particular, to implantable medical devices and systems having radio transmitters and antenna assemblies.

BACKGROUND

Implantable devices and systems are utilized in modern medicine to provide a host of diagnostic and/or therapeutic benefits. For example, implantable shunting systems are widely used to treat a variety of patient conditions by shunting fluid from a first body region/cavity to a second body region/cavity. The flow of fluid through the shunting systems is primarily controlled by the pressure gradient across the shunt lumen and the geometry (e.g., size) of the shunt lumen. One challenge with conventional shunting systems is selecting the appropriate geometry of the shunt lumen for a particular patient. A lumen that is too small may not provide enough therapy to the patient, while a lumen that is too large may create new issues in the patient. Despite this, most conventional shunts cannot be adjusted once they have been implanted. Accordingly, once the system is implanted, the therapy provided by the shunting system cannot be adjusted or titrated to meet the patient's individual needs.

As a result of the above, shunting systems with adjustable lumens have recently been proposed to provide a more personalized or titratable therapy. Such systems enable clinicians to titrate the therapy to an individual patient's needs, as well as adjust the therapy over time as the patient's disease changes. Some adjustable shunting systems include radio transmitters and antenna assemblies that allow clinicians to non-invasively communicate with the systems. It would be desirable to have a diverse set of communication options available to non-invasively communicate with an implanted device—for example, to provide energy to a device, to at least partially control the operation of the device, to extract information from the device, etc. However, previously disclosed devices and methods have challenges with accommodating the space and power requirements associated with the components required to achieve this diverse and multifaceted system communication paradigm, and often add complexity to the system that increases the system's overall size and weight and creates elevated risk of system failure.

BRIEF DESCRIPTION OF THE DRAWINGS

Many aspects of the present technology can be better understood with reference to the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

DETAILED DESCRIPTION

Figure 1:
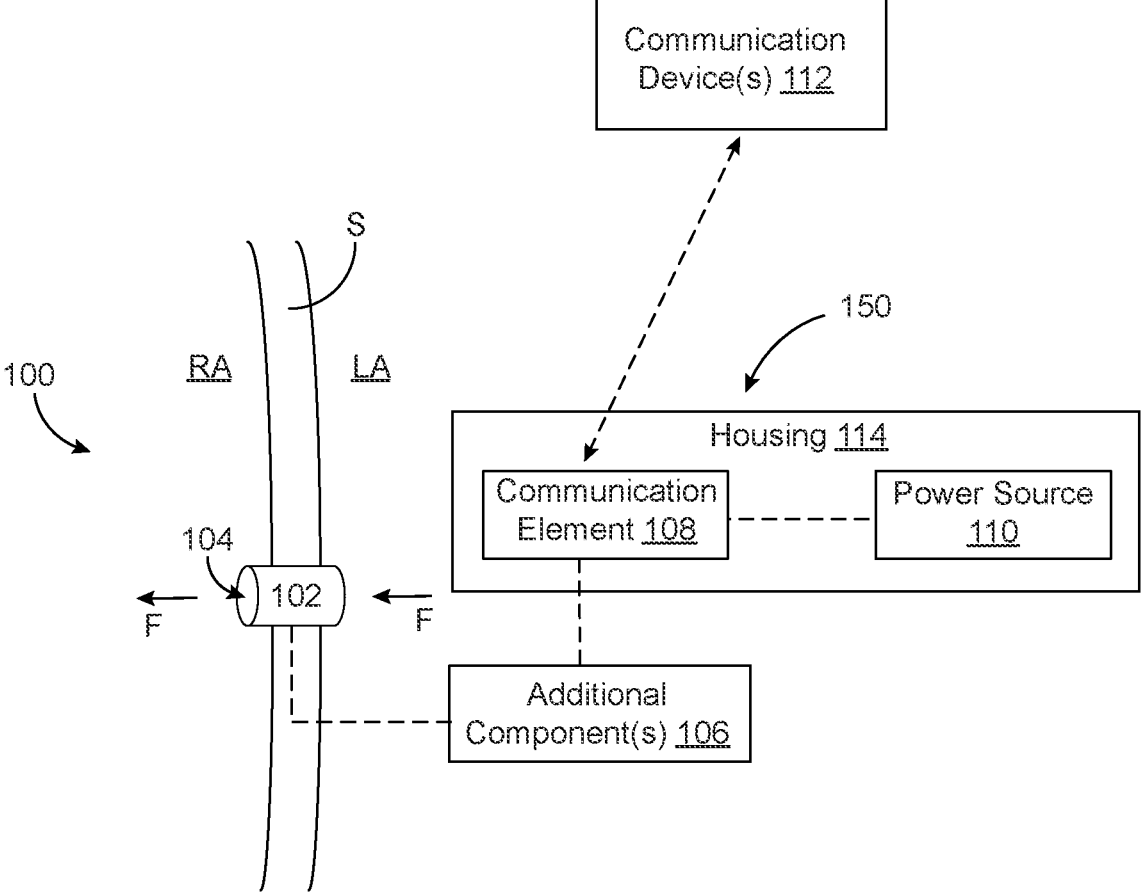
FIG. 1 is a schematic illustration of an interatrial device implanted in a heart of a patient and configured in accordance with select embodiments of the present technology.

The present technology is directed to implantable medical devices including one or more communication elements configured to transmit and/or receive communication signals from a source external to the implanted device (e.g., from a source external to a patient, from a separate device implanted within the patient, etc.). The communication element(s) can be operably coupled to one or more components of the device, such as an actuation element, an engine, a data storage/memory component, an energy storage component, a microcontroller, or a sensor. Accordingly, the communication element(s) can be used to transmit and/or receive signals between the implanted device and/or a device or user (e.g., a clinician) external to the patient. In at least some embodiments of the present technology, the communication elements can be used to transmit and/or receive signals related to the control of (e.g., operations, commands, etc.) the implanted device. In at least some embodiments of the present technology, the communication elements can be used to transmit and/or receive information (e.g., data, sensor measurements, device information, etc.) to or from one or more of the device components. In at least some embodiments, the communication element(s) can additionally be electrically coupled to a power source/ energy storage component and used to transfer energy to device components (e.g., from the power source to a sensor), and/or to transfer operational signals from a first device component to a second device component (e.g., from a microcontroller to an engine). In at least some embodiments, the communication element(s) can be configured to perform a first function at a first (e.g., relatively higher) frequency or frequency range, and to perform a second function at a second (e.g., relatively lower) frequency or frequency range. For example, in the first frequency range, the communication element(s) can be configured to transmit or transfer a communication signal, and in the second frequency range, the communication element(s) can be configured to transfer energy and/or operational signals. In some embodiments the communication element(s) can perform the first and second functions at a same or different time, e.g., coextensively and/or independently of each other.

In some embodiments, the implantable medical systems described herein include a first implantable device, a second implantable device, and a communication assembly extending therebetween and physically coupling the first device and the second device. The first device can include one or more first electronic components, such as an actuation element, an engine, a data storage/memory component, an energy storage component, a microcontroller, or a sensor. The second device can include one or more second electronic components, such as an actuation element, an engine, a data storage/memory component, an energy storage component, a microcontroller, or a sensor. The communication assembly can include (a) one or more first wires that are configured to wirelessly receive data from, and/or wirelessly transmit data to, a third device positioned external to the patient, and (b) one or more second wires that are configured to conductively transfer power between at least one of the one or more first electronic components in the first device and at least one of the one or more second electronic components in the second device. The first and second wires can extend along a length of the communication assembly between the first device and the second device. In some embodiments, the one or more first wires have a helical configuration, and the one or more second wires have a linear and/or braided configuration and extend within the one or more first wires (e.g., within the helix formed by the one or more first wires).

In one embodiment, the one or more communication elements and/or communication assemblies are implemented in a cardiovascular treatment device such as an interatrial shunt or implantable pressure sensor. The shunt for example, may be configured for shunting fluid between a first body region (e.g., a left atrium) and a second body region (e.g., a right atrium) of a patient. The system further includes a shunting element having a lumen extending therethrough that is configured to fluidly couple the first and second body regions when the shunting element is implanted in the patient. The system can also include an actuation element (e.g., a shape memory actuation element) configured to adjust a geometry of the lumen to change the flow of fluid therethrough. Examples of an actuation element for modifying the shunt are described in U.S. patent application Ser. Nos. 16/840,108 and 17/016,192, the entire contents of which are incorporated by reference herein for all purposes. The system can further include a communication element and/or assembly for transmitting and/or receiving communication and/or power signals. The communication element can be operably coupled to the actuation element such that a clinician can send a communication signal to the communication element to directly (e.g., via supplying energy) or indirectly (e.g., by providing instruction to a microprocessor that subsequently activates another aspect of the system) adjust the geometry of the lumen. In some embodiments, the communication element can be operably coupled to one or more sensors, engines, storage/memory components, energy storage components, microcontrollers, and/or other components of the device. For example, in at least some embodiments the communication element can be operably coupled to a pressure sensor positioned in the first body region such that the communication element can transmit pressure measurements from the pressure sensor to a user (e.g., clinician). In other embodiments, the communication element can be operably coupled to a memory and/or a microprocessor configured to store information (e.g., pressure measurements) from a pressure sensor, and the stored information can be transmitted from the memory and/or the microprocessor to a user (e.g., clinician) via the communication element. Additionally, in at least some embodiments the communication element can be coupled to a power source of the device such that the communication element can transmit information related to the power source (e.g., power level, charge status, etc.). Moreover, in at least some embodiments, the communication element can be configured to transfer energy from the power source/energy storage component to one or more device components, such as the pressure sensor. Furthermore, in at least some embodiments the communication element can be configured to transfer one or more operational signals, e.g., from a first component to a second component.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1-4C.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Throughout this specification, "power" and "energy" are used somewhat interchangeably. One of ordinary skill in the art will appreciate, however, that power and energy are not always equivalent. For example, a battery can viewed as both an "energy" storage or "power" storage component. However, "power" may also refer to a rate at which stored energy is discharged. Thus, one of ordinary skill in the art will understand that the terms "power" and "energy" may have a same or different meaning in various places throughout this specification based the context and/or manner in which these terms are used.

This specification also describes transmitting or transferring "power" and "data" between various components. As one skilled in the art will appreciate, both "power" and "data" can be transferred in various modalities, including the same modalities. For example, both power and data can be transferred wirelessly via electromagnetic radiation (e.g., via radiofrequency waves). Power and data can also be transferred conductively (e.g., via electricity). Accordingly, the use of "power transfer" and "data transfer" and similar variants does not, by itself, dictate a particular modality of transfer, but rather refers to the purpose of the energy transfer. For example, in many embodiments "power transfer" refers to transferring energy from an energy source to an energy storage component, or from an energy source to an active electronic component to power operation thereof, while "data transfer" refers to transferring energy in a manner that transfers information, e.g., beyond just merely powering a component.

FIG. 1 is a schematic illustration of a medical device system 100 ("the system 100") including one or more communication elements configured in accordance with an embodiment of the present technology. The system 100 includes a shunting element 102 defining a lumen 104 therethrough. In the illustrated embodiment, the shunting element 102 is implanted across a septal wall S in a patient's heart, although the shunting element 102 can be implanted in other regions of the body to fluidly connect any two body regions. When implanted across the septal wall S, the system 100 can fluidly connect a left atrium LA and a right atrium RA of the heart via the lumen 104. Accordingly, when the shunting element 102 is implanted in the septal wall S of some patients, blood can flow between the left atrium LA to the right atrium RA via the lumen 104 (as shown by arrows F). The system 100 can further include one or more additional components 106 that can be coupled to the shunting element 102. Some of the additional component(s) 106 can include features implanted with the shunting element 102 that require power to operate (i.e., active components). For example, active components can include one or more actuation elements (e.g., for adjusting a geometry or other characteristic of the shunting element 102), an engine, a storage/memory, a microcontroller, a sensor (e.g., for measuring one or more physiological parameters and/or one or more parameters of the system 100), and other components. The shunting element 102 can include additional features not shown in FIG. 1, including inactive components such as a frame, membrane, or the like.

The system 100 can further include a communication element 108 and a power source 110. As explained in greater detail below with reference to FIGS. 2A-3, the communication element 108 can couple (e.g., electrically, operatively, communicatively, etc.) the power source 110 and the additional component(s) 106, such that communication element 108 can transfer or convey energy from the power source 110 to the additional component(s) 106. Additionally, the communication element 108 can be configured to transmit and/or receive communication signals (e.g., information, data, commands, etc.). For example, the communication element 108 can transmit a communication signal from the additional component(s) 106 and/or the power source 110 to a device or user (e.g., a clinician) external to a patient. In at least some embodiments, the communication element 108 can transmit operational signals from a first device component (e.g., a sensor) to a second device component (e.g., a motor, a microprocessor, an actuation element, a shape memory actuation element, etc.). In at least some embodiments, the communication element 108 can include components such as wires, antennae, transmitters, transceivers, and/or any other suitable components.

The power source 110 can be or include a battery (e.g., a lithium-ion battery, a lithium primary battery, a zinc-ion battery, an alkaline battery, and/or any other suitable battery or cell), a supercapacitor, a capacitor, and/or one or more inductive elements configured to receive and/or store energy from an energy transmission device. Examples of systems that implement power-receiving inductive elements are described in U.S. Provisional Patent App. No. 63/093,073, filed Oct. 16, 2020, the entire contents of which is incorporated by reference herein for all purposes.

In some embodiments, one or more communication devices 112 can communicate (e.g., interact, control, monitor, exchange data, transfer data, etc.) with the system 100. The communication device(s) 112 can be positioned external to the system 100, e.g., such that a user (e.g., a clinician) can use the communication device(s) 112 to communicate with the system 100 when the system 100 is implanted in a patient. In some embodiments the communication device(s) 112 can be positioned inside of the patient but be separate from the system 100 and/or one or more of the components of the system 100 (e.g., the shunting element 102, the additional component(s) 106, the housing 114, etc.). In some such embodiments, the internally-located communication device(s) 112 can be positioned in a same or different anatomical region of the body relative to system 100. In some embodiments, multiple communication device(s) 112 can be included, and the communication element 108 can be configured to communicate with each of the multiple communication devices 112 directly, and/or the communication element 108 can be configured to communicate with a first communication device as part of a communication chain that includes one or more additional communication devices (i.e., the first communication device communicates with both the system 100, via the communication element 108, and the additional communication device(s), but the additional communication device(s) communicate with the first communication device and does not communicate with system 100 directly).

The communication device(s) 112 can be configured to communicate with the communication element 108, including transmitting communication signals to the communication element 108 and/or receiving communication signals from the communication element 108. The communication device(s) 112 can include any device or system external to the implant that is capable of wirelessly transmitting communication signals to an implanted component. For example, the communication device 112 and/or the communication element 108 can be configured to transmit and/or receive radiofrequency (RF) energy, microwave frequency energy, other forms of electromagnetic energy, ultrasonic energy, thermal energy, or other types of energy in accordance with techniques known to those of skill in the art. In some embodiments, the communication device 112 and/or the communication element 108 may operate in a frequency range between about 1 MHz and about 1 GHz, such as between about 900 MHz and about 930 MHz (e.g., 900 MHz, 901 MHz, 902 MHz, 903 MHz, 904 MHz, 905 MHz, etc.), between about 910 MHz and about 920 MHz, and/or about 915 MHz, although other frequencies are possible.

In at least some embodiments, one or more aspects of the system 100 can be combined in a device 150. The device 150 can include a can or housing 114 configured to contain (e.g., house, carry, encapsulate, etc.) one or more elements of the system 100. For example, in at least some embodiments the housing 114 can contain the communication element 108, the power source 110, and/or one or more of the additional components(s) 106 (e.g., one or more sensors, microcontroller, engines, memory, and/or actuation elements). In at least some embodiments, one or more of the elements of the systems 100 can have separate or individual housings.

The housing 114 and/or the device 150 can be placed within a catheter (not shown) and used to deliver the shunting element 102, communication element 108, the power source 110, and/or one or more of the additional components 106 to a target site within the patient. The housing 114 and/or the device 150 can be coupled (e.g., mechanically) to the shunting element 102, at least partially embedded in the septal wall S, and/or positioned at least partially in the first body cavity (e.g., the left atrium) and/or the second body cavity (e.g., the right atrium). In at least some embodiments, the system 100 can include a plurality of devices, wherein each of the devices can include a housing, and one or more of the communication element 108, the power source 110, and/or the additional component(s) 106 can be distributed and/or shared amongst the plurality of devices. For example, in at least some embodiments the communication element 108 can couple (e.g., mechanically, electrically, operatively, communicatively, etc.) a first device to one or more other devices.

As will be understood by one of skill from the description herein, the communication element 108 can be formed from a variety of materials including, but not limited to metals, alloys, and any other suitable material. The shape and configuration of the communication element 108 may be determined based on the material properties, delivery technique, and/or requirements of the application. The configuration of the communication element 108 will be described in more detail below.

Figure 2A:
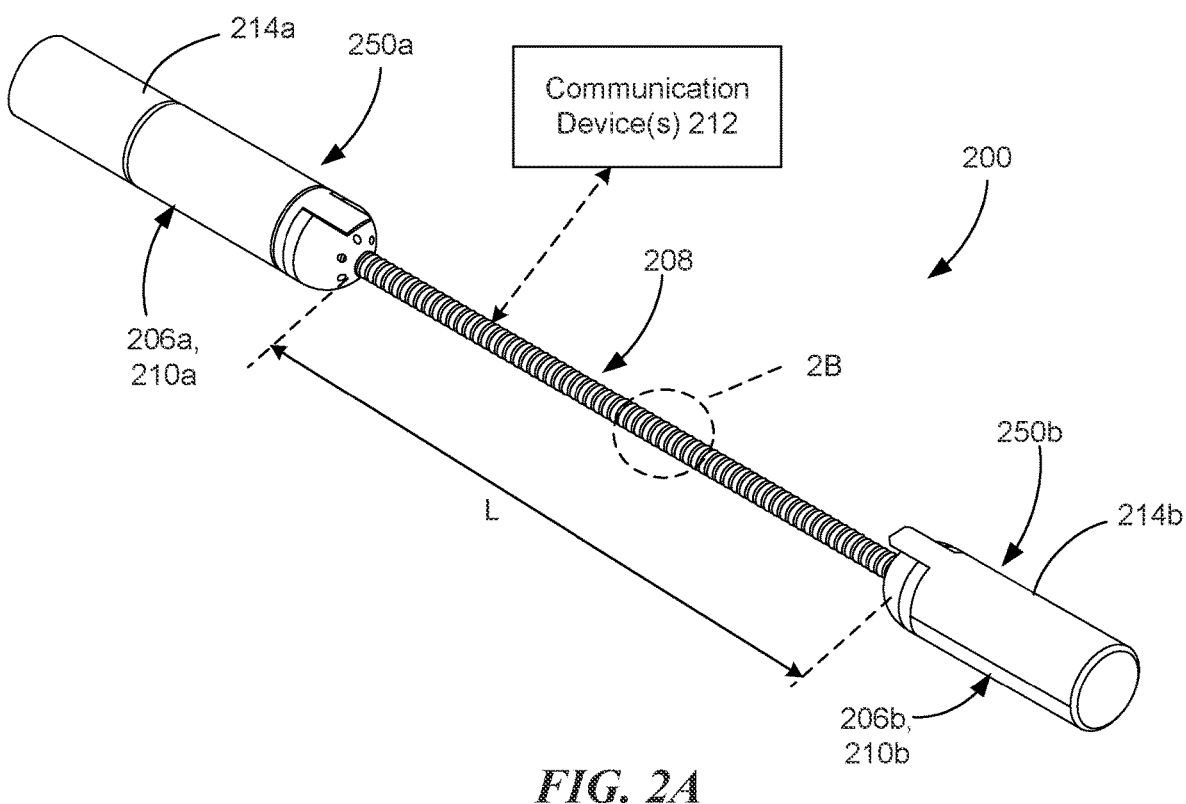
FIG. 2A is a perspective view of a first device coupled to a second device via a communication element configured in accordance with select embodiments of the present technology.
Figure 2B:
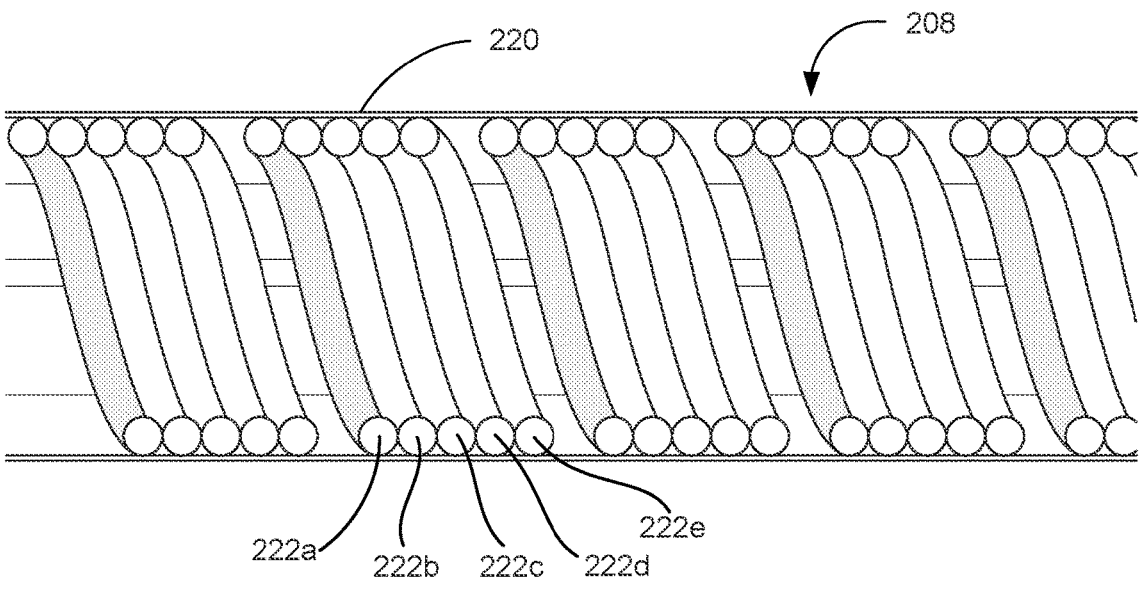
FIG. 2B is a side cross-sectional view of the communication element of FIG. 2B.

FIGS. 2A and 2B illustrate view of a system 200 configured in accordance with select embodiments of the present technology. The system 200 and/or one or more components thereof can be generally similar or the same as the system 100 of FIG. 1. Accordingly, like numbers are used to designate like components (e.g., communication element 208 versus communication element 108 of FIG. 1). In FIGS. 2A and 2B a number of system aspects have been omitted for clarity, and the following discussion of FIGS. 2A and 2B will be limited to those features that are different from system 100 and/or are necessary for context.

FIG. 2A illustrates a perspective view of a first subassembly or device 250a and a second subassembly or device 250b configured in accordance with select embodiments of the present technology. The first device 250a can include one or more first component(s) 206a and/or a first power source 210a positioned within a first can or housing 214a. Similarly, the second device 250b can include one or more second component(s) 206b and/or a second power source 210b positioned within a second can or housing 214b.

The first device 250a can be coupled (e.g., mechanically, electrically, communicatively, operably, etc.) to the second device 250b via a communication element 208. As described previously, the communication element 208 can be configured to transmit and/or receive communication signals from a communication device(s) 212. Additionally, and as described previously, the communication element 208 can be configured to connect the one or more first component(s) 206a and/or the first power source 210a to the one or more second component(s) 206b and/or the second power source 210b, e.g., to transfer power from a power source to one or more components and/or to transfer operational signals from a first component to a second component.

The communication element 208 can have a length L such that the first device 250a and the second device 250b are spaced apart from each other by the length L when arranged in the configuration shown in FIG. 2A. In some embodiments, the communication element 208 can be flexible and be bent or otherwise arranged such that the first device 250a and the second device 250b can be positioned closer to one another than the length L while retaining a communication path distance between the devices equal to the length L. In at least some embodiments, the length L can correspond to a wavelength at which the communication element 208 is configured to transmit and/or receive communication signals from the communication device(s) 212. In at least some embodiments, the length L can be selected to account for alterations of one or more characteristics (e.g., wavelength, frequency, etc.) of the communication signals that is associated with their travel through one or more media (e.g., blood) or environments (e.g., the left atrium and/or right atrium), e.g., the media/environment in which the system 200 will be operating. For example, in at least some embodiments, the length L of the communication element 208 corresponds to the electromagnetic wavelength in blood of an about 915 MHz radiofrequency signal, or any of the other frequencies or frequency ranges described herein. Accordingly, the length L can be selected such that the communication element 208 can be configured to operate as an electromagnetic antenna and/or transmitter at about a 915 MHz signal, or any of the other frequencies or frequency ranges described above (e.g., between about 900 MHz and about 930 MHz, between about 910 MHz and about 920 MHz, etc.).

In some embodiments, insulating materials with a particular dielectric constant may be incorporated in the communication element 208 in order change the frequency that a particular length L corresponds to, and thereby allow for additional selective adjustments for sizing of the system 200. For example, an insulating material such as polyurethane, silicone rubber, or polytetrafluoroethylene with a dielectric constant in the range of 1-5 (e.g., 1.5, 2.5, 3.5, or 4.5) could be added as a jacket on the communication element 208. In such an arrangement, the effective length L (which, as discussed above, corresponds to a wavelength at which the communication element 208 is configured to transmit and/or receive communication signals) can be increased by about 1-20%. In other embodiments, the effective length L of the communication element 208 corresponds to the acoustic wavelength in blood of an about 50 kHz ultrasonic signal. Accordingly, the effective length L can be selected such that the communication element 208 can be configured to operate as an acoustic resonator at about a 50 kHz signal.

In some embodiments, the length L can be between about 0.5 cm and about 20 cm, such as at least 1 cm, 2 cm, or 4 cm or any other suitable length. In some embodiments, the communication element 208 has a total length L but additionally or alternatively has one or more sub-sections smaller than the total length L configured to operate as an antenna and/or transmitter. These one or more subsections can correspond different wavelengths of communication signals. Accordingly, such embodiments can enable multi-frequency and/or multi-source communications between a communication element 208 and communication device(s) 212 and/or other components. In some embodiments, communication element 208 can operate both as an electromagnetic antenna and an acoustic resonator.

FIG. 2B is a side cross-sectional view of region 2B of communication element 208 of FIG. 2A. In the illustrated embodiment, the communication element 208 includes one or more leads or wires 222 surrounded by an insulating layer 220. Each of the wires 222 can couple the one or more first component(s) 206a and/or the first power source 210a to the one or more second component(s) 206b and/or the second power source 210b (FIG. 2A). Additionally, at least one of the wires 222 can be configured to transmit and/or receive communication signals from the communication device(s) 212. For example, in the illustrated embodiment, the first wire 222a is configured to transmit power and/or operational signals between the first and second devices 250a-b, and can be additionally configured to transmit and/or receive communication signals between the first and/or second devices 250a-b and the external communication device(s) 212. As described in greater detail below, the function or operation performed by the first wire 222a can vary based on a frequency of a signal provided to the first wire 222a.

In the illustrated embodiment, the communication element 208 includes a first wire 222a, a second wire 222b, a third wire 222c, a fourth wire 222d, and a fifth wire 222e (referred to collectively as "the wires 222"). In other embodiments, the communication element 208 can include more or fewer wires 222, such as one, two, three, four, six, seven, eight, or more wires 232. Additionally, in the illustrated embodiments the wires 222 are coiled or wrapped in a helical configuration. In other embodiments, however, the wires 222 can be bundled, packaged, wrapped, and/or otherwise stored in any suitable configuration.

Figure 3:
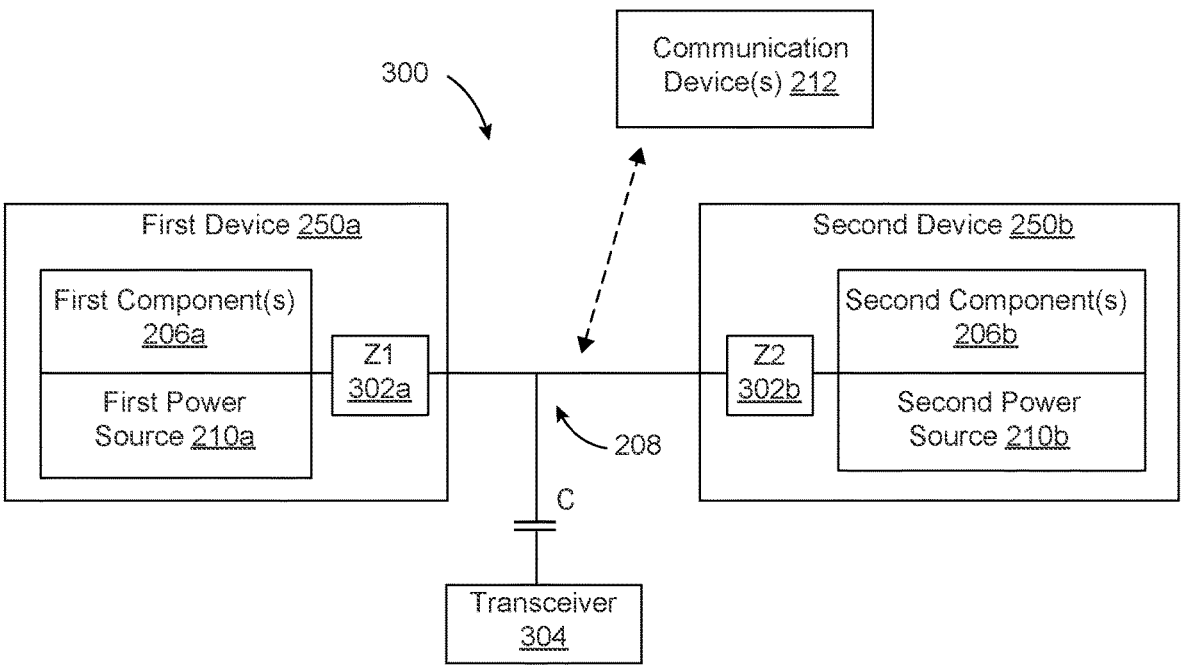
FIG. 3 is a schematic illustration of a system including a communication element and configured in accordance with select embodiments of the present technology.

FIG. 3 is a schematic illustration of a system 300 including the communication element 208 and configured in accordance with select embodiments of the present technology. Referring to FIGS. 2A-3 together, the system 300 can include a first element 302a having a first impedance Z1, a second element 302b having a second impedance Z2, and a capacitor C. In some embodiments, the transceiver 304 and capacitor C can be part of the first device 250a or the second device 250b. In such embodiments, the coupling between the transceiver 304 and the communication device(s) 212 can be incorporated in the first components 206a and/or the second components 206b. In other embodiments, there may be a first transceiver 304 and capacitor C in the first device 250a and a second transceiver 304 and capacitor C in the second device 250b. In such embodiments, the first and second transceivers can be coupled through respective capacitors C to either the same or different elements within the communication device 212. In other embodiments, the communication element 208 can couple (e.g., electrically, mechanically, etc.) the first element 302a, the second element 302b, and the capacitor C. Each of the first and second elements 302a-b can have a relatively high impedance at high frequencies, and a relatively low impedance at low frequencies. The first and second elements 302 a-b can include, for example, inductors, lossy ferrites, a combination thereof, or any other suitable component with these properties as would be known to one skilled in the art. In contrast, the capacitor C can have a relatively low impedance at high frequencies, and a relatively high impedance at low frequencies. In some embodiments, the capacitor C can be replaced with other elements having similar frequency properties, for example a gyrator connected to an inductor, or any other suitable elements and/or circuits with these properties as would be known to one skilled in the art.

In the illustrated embodiment, the first device 250 includes the first element 302a, and the first element 302a can be coupled to the first component(s) 206a and/or the first power source 210a. Similarly, in the illustrated embodiment the second device 250b includes the second element 302b, and the second element 302b can be coupled to the second component(s) 206b and/or the second power supply 210b. Additionally, the capacitor C can be coupled (e.g., electrically) to one or more radio or transceiver elements 304. The transceiver element(s) 304 can be configured to transmit and/or receive communication signals via the communication element 208, e.g., to communicate with a communication device(s) 212. The transceiver element(s) 304 can be coupled to (e.g., electrically, mechanically, etc.) and/or part of the first and/or second devices 250a-b. For example, in at least some embodiments, the first device 250a includes a first transceiver element coupled to the corresponding first component(s) 206a and/or first power source 210a, and the second device 250b includes a second transceiver element coupled to the corresponding second component(s) 206b and/or second power source 210b. In at least some embodiments, the transceiver element(s) 304 can be in communication (e.g., electrically coupled) with the first and/or second devices 250a-b, and/or one or more components thereof, such that the transceiver element(s) 304 can be used to transmit information related to the first and/or second devices 250a-b to the communication device(s) 212.

The first and second component(s) 206a-b and the first and second power sources 210a-b can be configured to transmit and/or receive energy and/or operational signals at relatively low frequencies. For example, the energy and/or operational signals can include frequencies in a range between about 0 MHz (e.g., for DC power) and about 500 MHz, such as between about 1 MHz and about 15 MHz (e.g., 1 MHz, 2 MHz, 3 MHz, 4 MHz, 5 MHz, 6 MHz, etc.), although other frequencies are possible. The transceiver element 304 can be configured to transmit and/or receive communication signals at relatively high frequencies. For example, the communication signals can include frequencies such as between about 900 MHz and about 930 MHz (e.g., 900 MHz, 901 MHz, 902 MHz, 903 MHz, etc.), between about 910 MHz and about 920 MHz, and/or about 915 MHz, although other frequencies are possible. In some embodiments, the operational signals can include frequencies in a range between about Hz and the communication signals. Accordingly, based on the relative impedances of the first element 302a, the second element 302b, and the capacitor C, the communication element 208 can be configured to perform a first function at a first (e.g., relatively higher) frequency or frequency range, and to perform a second function at a second (e.g., relatively lower) frequency or frequency range. For example, the impedances of the first and second elements 302a-b can at least partially prevent or impede first (e.g., high) frequency signals from reaching the first and/or second devices 250a-b. Accordingly, at the first frequencies the communication element 208 can be configured to perform a first function, e.g., to operate as an antenna for the transceiver 304 to communicate with the communication devices 212. Similarly, the impedance of the capacitor C can at least partially prevent or impede second (e.g., low) frequency signals from reaching the transceiver 304. Accordingly, at the second frequencies the communication element 208 can be configured to perform a second function, e.g., to transfer power and/or operational signals between the first and second devices 250a-b and/or one or more components thereof.

The system 300 can be configured such that the communication element 208 can perform the first and second functions at a same or different time. For example, the difference between the first and second frequencies or frequency ranges can be such that the communication element 208 can communicate with the communication device(s) 212 and transfer energy and/or operational signals between the first and second devices 250a simultaneously. This can include, for example, a difference of at least 0 Hz, 1 Hz, 10 Hz, 100 Hz, 1 kHz, 1 MHz, 1 GHz and/or any other suitable difference. Accordingly, the communication element 208 can be configured to operate in response to a plurality of signals concurrently, including a first higher frequency signal and a second relatively lower frequency signal.

As one skilled in the art will appreciate, communication elements configured in accordance with the present technology (e.g., communication element 208) can be incorporated in other electrical systems beyond those illustrated in FIG. 3. For example, the communication element (s) 208 can be incorporated into a conventional RLC circuit that provides energy to an energy storage device (e.g., a supercapacitor, a battery, etc.), which can subsequently release the stored energy to power an active component (e.g., motor, shape memory actuation element, sensor, etc.).

Figure 4A:
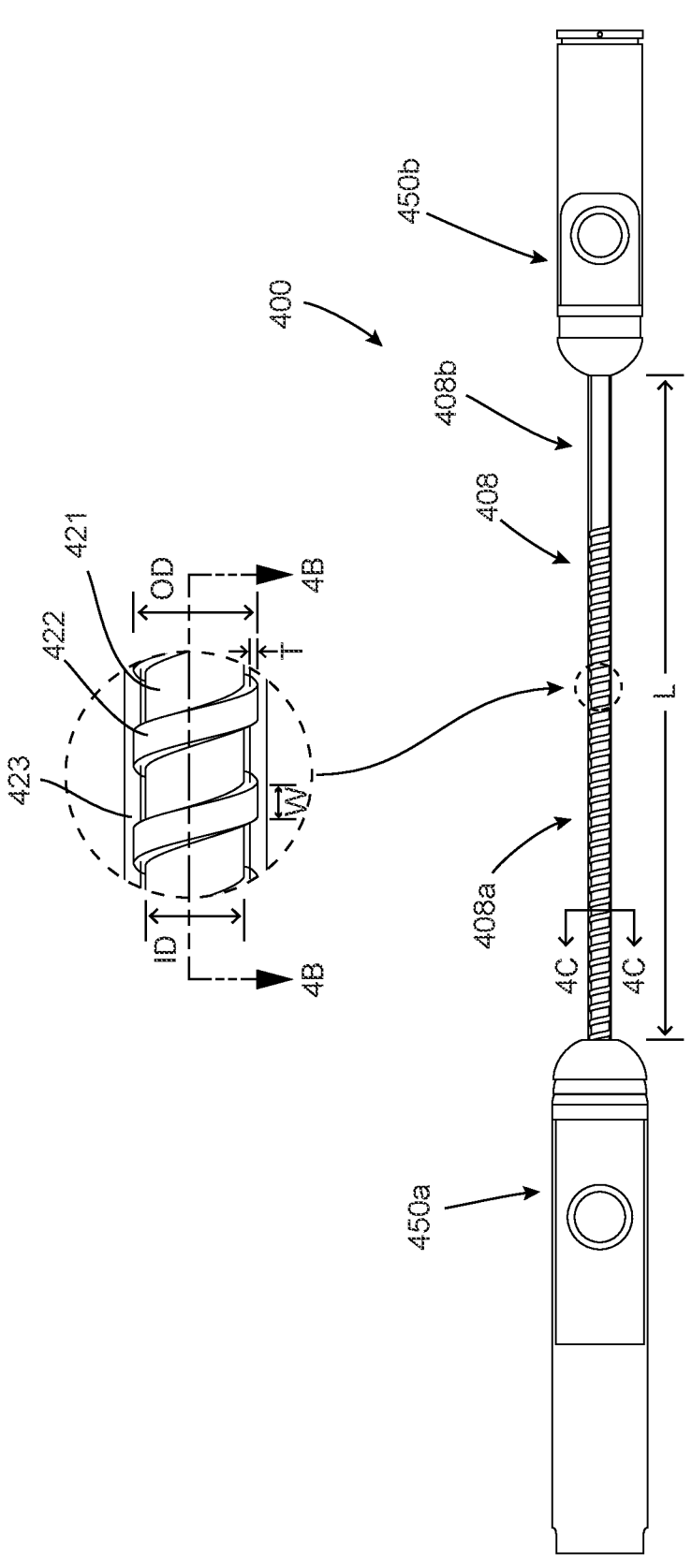
FIG. 4A is a side view of a system including a first device coupled to a second device via a communication assembly and configured in accordance with select embodiments of the present technology.

The present technology further includes communication elements/antenna assemblies similar to those described above for physically linking two distinct devices or canisters, but that have distinct structural components for performing different functions. For example, FIG. 4A illustrates a side view of a system 400 including a first subassembly or device 450a, a second subassembly or device 450b, and a communication assembly 408 (which can also be referred to as an antenna assembly 408, a communication element 408 or a tethering assembly 408) extending therebetween. The first device 450a and the second device 450b can be generally similar to or the same as the first device 250a and the second device 250b, respectively, described above with reference to FIGS. 2A and 3. For example, the first device 450a and/or the second device 450b can each include a hermetically sealed canister that houses various active and/ or electronic components of the system 400. As a particular example, the first device 450a can include a physiologic sensor (e.g., electronics associated with a physiologic sensor), and the second device 450b can include an energy storage component such as a battery or capacitor, although other configurations are possible and within the scope of the present technology. For example, the first device 450a and/or the second device 450b can include a memory, a microcontroller, a processor, an actuator, or other electrically active components.

Similar to the embodiment described above with reference to FIGS. 2A and 2B, the first device 450a can be physically coupled to the second device 450b via the communication assembly 408. However, unlike the communication element 208 described with reference to FIGS. 2A and 2B, the communication assembly 408 can include two or more discrete electronic components having different shapes and sizes each designed (e.g., optimized) for performing different functions. For example, the communication assembly 408 can include one or more first wires 422 (which can also be referred to herein as a first coil, transducer, antenna, or the like) having a generally helical pattern that extends partially or fully between the first device 450a and the second device 450b. As described below with reference to FIGS. 4B and 4C, the communication assembly 408 can also include one or more second wires 424 (which can also be referred to as conductors; not visible in FIG. 4A) that have a generally linear and/or braided pattern and that extend between the first device 450a and the second device 450b and within the first wire 422 (e.g., coaxially within an interior of the helix formed by the first wire 422). As described in detail below, the first wire 422 can be sized and shaped to wirelessly transmit power and/or data to, and/or wirelessly receive data and/or power from, a communication device or controller positioned external to the patient (e.g., the communication device 212 of FIG. 2A), while the one or more second wires 424 can be sized and shaped to conductively transmit power and/or data between the first device 450a and the second device 450b.

The communication assembly 408 can have a length L of, for example, between about 2.5 cm and about 7.5 cm, which can be selected based at least in part on the expected distance between the first device 450a and the second device 450b once the system 400 has been implanted within a patient. For example, the communication assembly 408 can have a length of between about 3 cm and about 7 cm, or between about 4 cm and about 6 cm, or about cm. In some embodiments the first wire 422 does not extend the full length of the communication assembly 408. That is, the first wire 422 extends along a first portion 408a of the communication assembly 408 that is less than the total length of the communication assembly 408. For example, the first wire 422 may extend between about 50% and about 95% of the length L of the communication assembly 408, and can therefore have a length of between about 1 cm and about 7 cm (e.g., the communication assembly 408 may have a length of 50 mm and the first wire 422 may have a length of about 38 mm). In other embodiments, the first wire 422 extends the full length, or substantially the full length, of the communication assembly 408, and therefore has the same or generally the same length as the communication assembly 408.

In some embodiments, the communication assembly 408 can be at least partially flexible along a portion of its length such that it can flex, bend, or otherwise deform to accommodate different positions of, and different spacing between, the first device 450a and the second device 450b. For example, the communication assembly 408 does not necessarily assume the illustrated linear configuration following implantation of the system 400—rather, in some embodiments, there may be one or more curves or bends in the communication assembly 408. In some embodiments, a second portion 408b of the communication assembly 408 that does not include the first wire 422 may be more flexible than the first portion 408a of the communication assembly 408 that includes the first wire 422, and therefore any curves or bends in the communication assembly 408 are generally positioned within the second portion 408b. Accordingly, providing a first wire 422 with a length that is less than the total length of the communication assembly 408 is expected to be advantageous for at least two reasons: (1) it permits the communication assembly 408 to be more flexible and therefore accommodate different spatial arrangements between the first device 450a and the second device 450b, and (2) it concentrates bends and other deformations within the second portion 408b of the communication assembly 408, which reduces the likelihood that the first wire 422 will be significantly deformed and interfere with potential data transfer to and from the first wire 422.

Referring to the enlarged portion of FIG. 4A, the first wire 422 is a ribbon antenna having a generally helical configuration. The first wire 422 is wrapped around a first or inner layer or sleeve of insulation 421 ("the inner insulation layer 421"), and positioned inside and/or embedded within a second or outer layer or sleeve of insulation 423 ("the outer insulation layer 423"). The inner insulation layer 421 and the outer insulation layer 423 can be composed of the same or different materials, and can be electrically and/or thermally insulating. The inner insulation layer 421 and the outer insulation layer 423 can also be composed of a biocompatible material. Example materials include, but are not limited to, urethanes (e.g., ChronoFlex C®, manufactured by AdvanSource Biomaterials of Wilmington, MA), polyurethanes, hydrocarbons (e.g., perylene), polytetrafluoroethylene (PTFE), expanded PTFE (ePTFE), or other suitable materials. In operation, the inner insulation layer 421 and the outer insulation layer 423 electrically and/or thermally insulate the first wire 422 from the second wires 424 (FIGS. 4B and 4C) and environment external to the communication assembly 408, respectively. Although shown as a single first wire 422, in some embodiments the communication assembly 408 includes more than one first wire 422, such as two, three, four, or more first wires 422. In such embodiments, the first wires 422 can be bundled together, soldered or crimped end-to-end, or have another suitable arrangement.

The first wire 422 can be sized and shaped to wirelessly receive and/or wirelessly transmit data and/or power to and/or from a communication device positioned external to the patient. In some embodiments, the first wire 422 is sized and shaped to wirelessly transmit and/or receive data at various operational parameters, such as at a frequency between about 1 MHz and about 1 GHz, or between about 500 MHz and 1 GHz, or between about 750 MHz and about 1 GHz, or between about 800 MHz and about 1 GHz, or between about 900 MHz and about 930 MHz (e.g., 900 MHz, 901 MHz, 902 MHz, 903 MHz, 904 MHz, 905 MHz, etc.), or between about 910 MHz and about 920 MHz, and/or about 915 MHz, although other frequencies are possible. In some embodiments, the first wire 422 is sized and shaped to operate within various ISM bands, such as the 915 and/or 868 ISM bands. The first wire 422 may form a helical path having a pitch between about 0.5 mm and about 4 mm, or between about 0.5 mm and about 2 mm, or between about 0.5 mm and about 1.5 mm, or about 1.0 mm. The helical path formed by the first wire 422 can have an outer diameter OD between about 0.8 mm and about 1.4 mm, or between about 0.9 mm and about 1.3 mm, or between about 1.0 mm and about 1.2 mm, or about 1.1 mm, and an inner diameter ID between about 0.7 mm and about 1.3 mm or between about 0.8 mm and about 1.2 mm, or between about 0.9 mm and about 1.1 mm, or about 1.0 mm. Accordingly, the first wire 422 may have a thickness T between about mm and about 2.5 mm, or between about 0.05 mm and about 2.0 mm, or between about mm and about 1.5 mm, or about 1.0 mm. The first wire 422 may also have a width W between about 0.1 mm and about 1 mm, or between about 0.1 mm and about 0.6 mm, or between about 0.2 mm and about 0.5 mm, or about 3.5 mm. The foregoing dimensions and ranges of dimensions are provided by way of example only—in some embodiments the first wire 422 can have dimensions outside the foregoing ranges. Indeed, as one skilled in the art will appreciate, the first wire 422 can be sized and shaped, and therefore tuned, to operate (e.g., transfer and/or receive data) at different frequencies and/or wavelengths.

The first wire 422 can be composed of a material that can transmit and/or receive data and/or power wirelessly. For example, the first wire 422 can be composed of solid silver, gold, or another suitable material. In some embodiments, the first wire 422 can have a core composed of a first material and an outer cladding or plating surrounding the core and that is composed of a second material. For example, the first material can include a metal or metal alloy such as Nitinol, steel, stainless steel, titanium, copper, or the like, and the second material can include silver, gold, or the like. In such embodiments, the first material can be selected to provide/ improve certain mechanical properties (e.g., durability, rigidity, etc.), while the second material can be selected to provide/improve certain electrical properties (e.g., wireless data transfer efficiency).

Figure 4C:
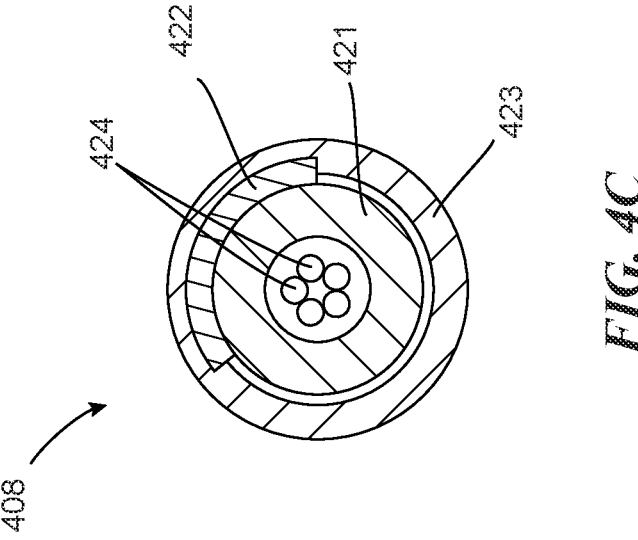
FIGS. 4B and 4C are cross-sectional views of portions of the system of FIG. 4A.
Figure 4B:
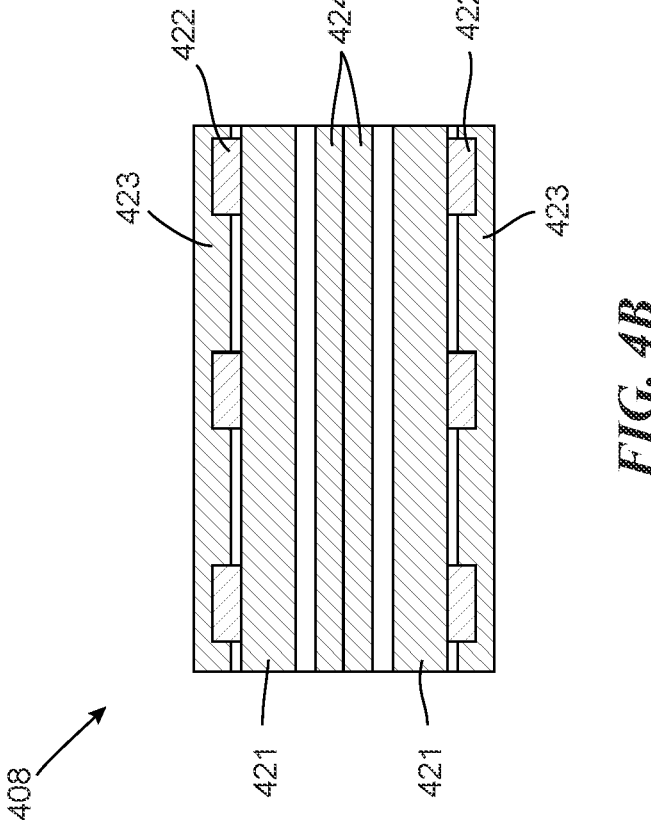

FIGS. 4B and 4C are cross sectional views of portions of the communication assembly 408 taken along the lines indicated in FIG. 4A. Referring collectively to FIGS. 4B and 4C, the second wires 424 extend coaxially within the inner insulation layer 421. As best seen in FIG. 4C, the illustrated embodiment includes five second wires 424, although in other embodiments the communication assembly 408 can have more or fewer second wires 424, such as one, two, three, four, six, seven, or eight. As set forth above, the second wires 424 can be configured to electrically connect the first device 450a and the second device 450b (FIG. 4A), such as to transfer power therebetween. Different second wires 424 can have different or similar functions, including, but not limited to, forming part of an inter-integrated circuit (I2C), acting as a voltage monitor, or the like.

Individual ones of the second wires 424 can be composed of the same or different material. In some embodiments, the second wires 424 can include an outer tubing material surrounding an inner core. The inner core can be composed of gold, silver, platinum, titanium alloys, Nitinol, tantalum, platinum alloys, tungsten, or other suitable elements and materials. The outer tubing material can be composed of Nitinol, titanium alloys, and other composite materials, such as 35N LT®, MP35N®, or FWM 1058®, manufactured by Fort Wayne Metals of Fort Wayne, Indiana. In some embodiments, each of the second wires 424 can be individually insulated and/or be composed of a plurality of strands (e.g., two, three, four, five, six, seven, or more strands) that are individually insulated. Further, in some embodiments two or more of the second wires 424 (e.g., pairs of second wires 424) can be twisted/braided, e.g., to reduce interference.

Without intending to be bound by theory, the communication assembly 408 is expected to be advantageous because it includes discrete structures that are specifically tuned (e.g., sized, shaped, and formulated) to achieve their respective functions. For example, the first wire 422 can be specifically constructed to more efficiently transmit data to, or receive data from, an external device, while the one or more second wires 424 can be specifically constructed to more efficiently transmit power between the first device 450a and the second device 450b. Moreover, by nesting the second wires 424 within the helical path of the first wire 422, the communication assembly 408 retains its advantageous low-profile configuration.

Communication elements configured in accordance with the present technology offer a number of advantages over technologies that are presently available. As described previously, traditional systems typically utilize radio transceivers having antennas disposed separately from other components of the system. Such an arrangement can add complexity to the system and increase the system's overall size and weight. In contrast with such conventional systems, devices configured in accordance with the present technology, which incorporates the antenna into a communication device which can also provide other aspects of the system (e.g., structural support, anatomical anchoring, and/or communication between a plurality of devices in the system) can be relatively smaller in size. This is expected to benefit patients by leaving more room around the implant (e.g., more room on a septal wall) to enable future procedures that require septal access or crossing (e.g., pulmonary vein ablation, mitral valve procedures, left atrial appendage closures, etc.), and/or allow for a smaller implant and, therefore, a smaller catheter delivery size, which increases the safety profile for patients. Moreover, devices configured in accordance with the presently disclosed technology are expected to be more robust to failure.

As will also be appreciated, various components of the systems described herein can be omitted without deviating from the scope of the present technology. Likewise, additional components not explicitly described above may be added to the systems without deviating from the scope of the present technology. Moreover, the communication elements described herein can be incorporated into other types of implantable medical devices beyond cardiac shunts. Accordingly, the present technology is not limited to the configurations expressly identified herein, but rather encompasses variations and alterations of the described systems.

EXAMPLES

Several aspects of the present technology are set forth in the following examples:
   1. A system for shunting fluid between a first body region and a second body region of a patient, the system comprising:

a shunting element configured to be implanted in the patient;

an actuation element configured to adjust a geometry of the lumen; and an electrical circuit including at least one communication element configured to— transmit and/or receive one or more communication signals to a communication device external to the patient at a first frequency range, and transfer power and/or one or more operational signals at a second frequency range different than the first frequency range.

2. The system of example 1 wherein the first frequency range is between about 910 MHz and about 920 MHz.

3. The system of example 2 wherein the communication element has a length that corresponds to the first frequency range.

4. The system of any one of examples 1-3 wherein the second frequency range is at least 1 Hz less than the first frequency range.

5. The system of any one of examples 1-3 wherein the second frequency range is at least 1 MHz less than the first frequency range.

6. The system of any one of examples 1-3 wherein the second frequency range is at least 1 GHz less than the first frequency range.

7. The system of any one of examples 1-6 wherein the communication element is configured to receive a plurality of signals simultaneously, and wherein the plurality of signals includes a first signal at the first frequency range and a second signal at the second frequency range.

8. The system of any one of examples 1-7, further comprising a first device and a second device, wherein the at least one communication element is configured to mechanically couple the first device and the second device.

9. The system of example 8 wherein the first device includes a first housing containing one or more first components and/or a first power source, and wherein the second device includes a second housing containing one or more second components and/or a second power source.

10. The system of example 9 wherein the communication element is configured to operably couple at least two of the following: (i) the one or more first components, (ii) the first power source, (iii) the one or more second components, and/or (iv) the second power source.

11. The system of example 10 wherein, at the second frequency range, the communication element is configured to transfer power and/or one or more operational signals between at least two of the following: (i) the one or more first components, (ii) the first power source, (iii) the one or more second components, and/or (iv) the second power source.

12. The system of any one of examples 1-11 wherein the at least one communication element includes a plurality of wires coiled or wrapped in a helical configuration.

13. The system of any one of examples 1-12 wherein:

the electrical circuit further includes a first element have a first impedance and coupled to the first device, a second element having a second impedance and coupled to the second device, and a capacitor coupled to a transceiver; and the at least one communication element is coupled to the first element, the second element, and the capacitor.

14. An electrical circuit for use with an implantable medical device, the electrical circuit comprising:

a communication element operably coupled to the implantable medical device, wherein the communication element comprises at least one wire configured to:

transmit and/or receive one or more communication signals to an external communication device at a first frequency range, and transfer power and/or one or more operational signals at a second frequency range.

15. The electrical circuit of example 14 wherein the first frequency range is between about 910 MHz and about 920 MHz.

16. The electrical circuit of example 14 or example 15 wherein the at least one wire has a length that corresponds to the first frequency range.

17. The electrical circuit of any one of examples 14-16 wherein the second frequency range is between about 0 Hz and the first frequency range.

18. The electrical circuit of any one of examples 14-16 wherein the second frequency range is 1 Hz less than the first frequency range.

19. The electrical circuit of any one of examples 14-16 wherein the second frequency range is 1 kHz less than the first frequency range.

20. The electrical circuit of any one of examples 14-16 wherein the second frequency range is 1 MHz less than the first frequency range.

21. The electrical circuit of any one of examples 14-16 wherein the second frequency range is 1 GHz less than the first frequency range.

22. The electrical circuit of any one of examples 14-21 wherein the at least one wire is configured to receive a plurality of signals simultaneously, wherein the plurality of signals includes a first signal at the first frequency range and a second signal at the second frequency range.

23. The electrical circuit of any one of examples 14-22, further comprising a first inductor coupled to a first device, a second inductor coupled to a second device, and a capacitor coupled to a transceiver, and wherein the at least one communication element is electrically coupled to the first inductor, the second inductor, and the capacitor.

24. An implantable medical device, comprising:

a plurality of wires, wherein the plurality of wires are configured to operably couple at least two of the following together: one or more first components, one or more second components, a first power source, and a second power source, and wherein at least one of the wires is additionally coupled to a transceiver and configured to— transmit and/or receive one or more communication signals to an external communication device at a first frequency range, and transfer power and/or one or more operational signals between at least two of: (i) the one or more first components, (ii) the first power source, (iii) the one or more second components, and/or (iv) the second power source at a second frequency range.

25. The device of example 24 wherein the first frequency range is between about 910 MHz and about 920 MHz.

26. The device of example 24 or example 25 wherein the at least one of the wires has a length that corresponds to the first frequency range.

27. The device of any one of examples 24-26 wherein the at least one of the wires is configured to receive a plurality of signals simultaneously, and wherein the plurality of signals includes a first signal at the first frequency range and a second signal at the second frequency range.

28. The device of any one of examples 24-27 wherein the plurality of wires are arranged in a helical configuration.

29. A method, comprising:

transmitting, at a first frequency range, one or more communication signals from a transceiver of an implantable medical device to a communication device external to a patient; and transmitting, at a second frequency range, one or more operational signals between a first component of the implantable medical device and a second component of the implantable medical device, wherein transmitting at the first and second frequency ranges includes transmitting via a communication element.

30. The method of example 29 wherein the first component and/or second component includes at least one of the following: an actuation element, an engine, a microcontroller, a sensor, and a power source.

31. The method of example 29 or example 30 wherein the communication signals are first communication signals, and wherein the method further comprises receiving via the transceiver at the first frequency range, one or more second communication signals from the communication device.

32. The method of any one of examples 29-31 wherein the first frequency range is between about 910 MHz and about 920 MHz.

33. The method of any one of examples 29-32 wherein the communication element has a length corresponding to the first frequency range.

34. The method of any one of examples 29-33 wherein the communication element is configured to transmit at the first and second frequency ranges simultaneously.

Conclusion

Embodiments of the present disclosure may include some or all of the following components: a battery, supercapacitor, or other suitable power source; a microcontroller, FPGA, ASIC, or other programmable component or system capable of storing and executing software and/or firmware that drives operation of an implant; memory such as RAM or ROM to store data and/or software/firmware associated with an implant and/or its operation; wireless communication hardware such as an antenna system configured to transmit via Bluetooth, WiFi, LoRa, Thread, Zigbee, UWB, or other protocols known in the art; energy harvesting means, for example a coil or antenna which is capable of receiving and/or reading an externally-provided signal which may be used to power the device, charge a battery, initiate a reading from a sensor, or for other purposes. Embodiments may also include one or more sensors, such as pressure sensors, impedance sensors, accelerometers, force/strain sensors, temperature sensors, flow sensors, optical sensors, cameras, microphones or other acoustic sensors, ultrasonic sensors, ECG or other cardiac rhythm sensors, SpO2 and other sensors adapted to measure tissue and/or blood gas levels, blood volume sensors, and other sensors known to those who are skilled in the art. Embodiments may include portions that are radiopaque and/or ultrasonically reflective to facilitate image-guided implantation or image guided procedures using techniques such as fluoroscopy, ultrasonography, or other imaging methods. Embodiments of the system may include specialized delivery catheters/systems that are adapted to deliver an implant and/or carry out a procedure. Systems may include components such as guidewires, sheaths, dilators, and multiple delivery catheters. Components may be exchanged via over-the-wire, rapid exchange, combination, or other approaches.

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments. For example, although this disclosure has been written to describe devices that are generally described as being used to create a path of fluid communication between the left atrium and the right atrium, it should be appreciated that similar embodiments could be utilized for shunts between other chambers of the heart or for shunts in other regions of the body.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An implantable medical system, the system comprising:

a first device carrying one or more first electronic components and configured to be implanted in a patient;

a second device carrying one or more second electronic components and configured to be implanted in the patient; and a communication assembly extending between and physically coupling the first device and the second device, wherein the communication assembly includes— one or more first wires having a helical configuration, wherein the one or more first wires are configured to wirelessly transmit and/or receive data, and one or more second wires having a linear configuration and extending within the one or more first wires, wherein the one or more second wires are configured to conductively transfer power from the one or more second electronic components to the one or more first electronic components.

2. The system of claim 1 wherein the communication assembly is flexible.

3. The system of claim 1 wherein the communication assembly has a length, and wherein the one or more first wires extend along less than the length of the communication assembly.

4. The system of claim 3 wherein the one or more first wires extend between about 50% and 95% of the length of the communication assembly.

5. The system of claim 1 wherein the communication assembly further comprises an insulation sleeve, and wherein:

the one or more first wires are wrapped around a radially outer surface of the insulation sleeve, and the one or more second wires extend coaxially within the insulation sleeve.

6. The system of claim 5 wherein the insulation sleeve is composed of a thermally insulative material.

7. The system of claim 5 wherein the insulation sleeve is composed of an electrically insulative material.

8. The system of claim 5 wherein the insulation sleeve is a first insulation sleeve, and wherein:

the communication assembly further comprises a second insulation sleeve, and the one or more first wires are positioned between the first insulation sleeve and the second insulation sleeve.

9. The system of claim 1 wherein the one or more second wires include at least two second wires.

10. The system of claim 1 wherein the one or more first wires have:

a pitch between about 0.5 mm and about 5 mm, an outer diameter between about 0.8 mm and about 1.4 mm, and an inner diameter between about 0.7 mm and about 1.3 mm.

11. The system of claim 1 wherein the one or more first wires include a ribbon wire.

12. The system of claim 8 wherein the one or more first wires are configured to wirelessly transmit and/or receive data within a first frequency range of from 800 MHz to 1 GHz.

13. The system of claim 1 wherein the one or more first electronic components include a sensor or a microcontroller, and wherein the one or more second electronic components include an energy storage component.

14. A method of operating an implanted medical device having a first canister housing one or more first electronic components and a second canister housing one or more second electronic components, the method comprising:

wirelessly transmitting data between the first canister and a controller positioned external to the patient via one or more first wires, wherein the one or more first wires have a helical configuration and extend at least partially between the first canister and the second canister; and conductively transmitting power from the one or more second electronic components to the one or more first electronic components via one or more second wires extending between the first canister and the second canister, wherein the one or more second wires have a linear configuration and extend within the one or more first wires.

15. The method of claim 14 wherein the one or more first electronic components include a sensor or a microcontroller, and wherein the one or more second electronic components include an energy storage component.

16. The method of claim 14 wherein wirelessly transmitting data between the first canister and the controller includes wireless transferring data within a frequency range of from 800 MHz to 1 GHz.

* * * * *